United States Patent
Draper et al.

(10) Patent No.: US 10,987,174 B2
(45) Date of Patent: Apr. 27, 2021

(54) PATIENT INTRODUCER ALIGNMENT

(71) Applicant: Auris Health, Inc., Redwood City, CA (US)

(72) Inventors: Jeffrey William Draper, San Francisco, CA (US); Sergio L. Martinez, Jr., Redwood City, CA (US); Ryan Jeffrey Connolly, San Carlos, CA (US); Allen Jiang, Fremont, CA (US); David Paul Noonan, San Francisco, CA (US); Douglas Bruce Dull, San Jose, CA (US)

(73) Assignee: Auris Health, Inc., Redwood City, CA (US)

( * ) Notice: Subject to any disclaimer, the term of this patent is extended or adjusted under 35 U.S.C. 154(b) by 31 days.

(21) Appl. No.: 15/935,955

(22) Filed: Mar. 26, 2018

(65) Prior Publication Data
US 2018/0289431 A1 Oct. 11, 2018

Related U.S. Application Data

(60) Provisional application No. 62/483,279, filed on Apr. 7, 2017.

(51) Int. Cl.
*A61B 34/20* (2016.01)
*A61B 34/30* (2016.01)
(Continued)

(52) U.S. Cl.
CPC ............. *A61B 34/20* (2016.02); *A61B 34/30* (2016.02); *A61B 90/11* (2016.02); *A61B 90/98* (2016.02);
(Continued)

(58) Field of Classification Search
CPC ........ A61B 2034/305; A61B 2034/304; A61B 2090/0808; B25J 19/02; B25J 19/026;
(Continued)

(56) References Cited

U.S. PATENT DOCUMENTS

| 3,763,860 A | 10/1973 | Clarke |
| 4,040,413 A | 8/1977 | Ohshiro |

(Continued)

FOREIGN PATENT DOCUMENTS

| EP | 1 321 106 | 6/2003 |
| EP | 1 849 423 | 10/2007 |

(Continued)

OTHER PUBLICATIONS

International Search Report and Written Opinion in application No. PCT/US/2018/024292, dated May 31, 2018.

(Continued)

*Primary Examiner* — Tan-Uyen T Ho
*Assistant Examiner* — Chima U Igboko
(74) *Attorney, Agent, or Firm* — Knobbe, Martens, Olson & Bear, LLP

(57) ABSTRACT

A patient introducer for use with a surgical robotic system is disclosed. In one aspect, the patient introducer may include an introducer tube extending between (i) a distal end connectable to a port and (ii) a proximal end configured to receive a surgical tool. The introducer tube may be configured to guide the surgical tool into the port. The patient introducer may also include an alignment member connected to the introducer tube and including a first shape and a first alignment marking. The alignment member may be configured to interface with a manipulator assembly of a robotic system. The manipulator assembly may include a second shape and a second alignment marking, the first shape being complementary to the second shape. The first (Continued)

alignment marking of the alignment member may facilitate rotational alignment of the alignment member and the manipulator assembly.

30 Claims, 16 Drawing Sheets

(51) Int. Cl.
  *A61B 90/98*  (2016.01)
  *A61B 90/00*  (2016.01)
  *A61M 25/01*  (2006.01)
  *A61B 90/57*  (2016.01)
  *A61B 17/00*  (2006.01)
  *A61B 90/11*  (2016.01)

(52) U.S. Cl.
  CPC .............. *A61B 2017/00477* (2013.01); *A61B 2017/00809* (2013.01); *A61B 2017/00876* (2013.01); *A61B 2034/2051* (2016.02); *A61B 2034/2055* (2016.02); *A61B 2034/2063* (2016.02); *A61B 2034/2065* (2016.02); *A61B 2034/301* (2016.02); *A61B 2034/303* (2016.02); *A61B 2090/0808* (2016.02); *A61B 2090/3937* (2016.02); *A61B 2090/571* (2016.02); *A61M 25/0127* (2013.01)

(58) Field of Classification Search
  CPC ........ B25J 19/027; B25J 19/028; B25J 19/04; B25J 19/063; B25J 19/068; A61M 25/0105; A61M 25/0108; A61M 25/0127
  See application file for complete search history.

(56) References Cited

U.S. PATENT DOCUMENTS

| | | |
|---|---|---|
| 4,198,960 A | 4/1980 | Utsugi |
| 4,470,407 A | 9/1984 | Hussein |
| 4,532,935 A | 8/1985 | Wang et al. |
| 4,685,458 A | 8/1987 | Leckrone |
| 4,747,405 A | 5/1988 | Leckrone |
| 4,854,301 A | 8/1989 | Nakajima |
| 4,898,574 A | 2/1990 | Uchiyama et al. |
| 4,983,165 A | 1/1991 | Loiterman |
| 5,029,574 A | 7/1991 | Shimamura et al. |
| 5,085,659 A | 2/1992 | Rydell |
| 5,196,023 A | 3/1993 | Martin |
| 5,217,465 A | 6/1993 | Steppe |
| 5,308,323 A | 5/1994 | Sogawa et al. |
| 5,318,589 A | 6/1994 | Lichtman |
| 5,325,848 A | 7/1994 | Adams et al. |
| 5,342,381 A | 8/1994 | Tidemand |
| 5,344,395 A | 9/1994 | Whalen et al. |
| 5,353,783 A | 10/1994 | Nakao et al. |
| 5,370,609 A | 12/1994 | Drasler et al. |
| 5,372,124 A | 12/1994 | Takayama et al. |
| 5,411,016 A | 5/1995 | Kume |
| 5,431,649 A | 7/1995 | Mulier et al. |
| 5,441,485 A | 8/1995 | Peters |
| 5,449,356 A | 9/1995 | Walbrink |
| 5,450,843 A | 9/1995 | Moll et al. |
| 5,472,426 A | 12/1995 | Bonati et al. |
| 5,496,267 A | 3/1996 | Drasler |
| 5,501,667 A | 3/1996 | Verduin, Jr. |
| 5,520,684 A | 5/1996 | Imran |
| 5,545,170 A | 8/1996 | Hart |
| 5,562,648 A | 10/1996 | Peterson |
| 5,562,678 A | 10/1996 | Booker |
| 5,572,999 A | 11/1996 | Funda et al. |
| 5,573,535 A | 11/1996 | Viklund |
| 5,613,973 A | 3/1997 | Jackson et al. |
| 5,645,083 A | 7/1997 | Essig et al. |
| 5,653,374 A | 8/1997 | Young et al. |
| 5,658,311 A | 8/1997 | Baden |
| 5,695,500 A | 12/1997 | Taylor et al. |
| 5,697,949 A | 12/1997 | Giurtino et al. |
| 5,710,870 A | 1/1998 | Ohm |
| 5,716,325 A | 2/1998 | Bonutti |
| 5,788,667 A | 8/1998 | Stoller |
| 5,792,165 A | 8/1998 | Klieman |
| 5,797,900 A | 8/1998 | Madhani |
| 5,810,770 A | 9/1998 | Chin et al. |
| 5,893,869 A | 4/1999 | Barnhart |
| 5,897,491 A | 4/1999 | Kastenbauer et al. |
| 5,924,175 A | 7/1999 | Lippitt |
| 5,989,230 A | 11/1999 | Frassica |
| 6,071,281 A | 6/2000 | Burnside et al. |
| 6,093,157 A | 7/2000 | Chandrasekaran |
| 6,110,171 A | 8/2000 | Rydell |
| 6,120,476 A | 9/2000 | Fung et al. |
| 6,120,498 A | 9/2000 | Jani et al. |
| 6,156,030 A | 12/2000 | Neev |
| 6,174,318 B1 | 1/2001 | Bates et al. |
| 6,183,435 B1 | 2/2001 | Bumbalough et al. |
| 6,206,903 B1 | 3/2001 | Ramans |
| 6,322,557 B1 | 11/2001 | Nikolaevich |
| 6,375,635 B1 | 4/2002 | Moutafis |
| 6,394,998 B1 | 5/2002 | Wallace et al. |
| 6,405,078 B1 | 6/2002 | Moaddeb et al. |
| 6,440,061 B1 | 8/2002 | Wenner et al. |
| 6,508,823 B1 | 1/2003 | Gonon |
| 6,522,906 B1 | 2/2003 | Salisbury et al. |
| 6,577,891 B1 | 6/2003 | Jaross et al. |
| 6,676,668 B2 | 1/2004 | Mercereau et al. |
| 6,685,698 B2 | 2/2004 | Morley et al. |
| 6,706,050 B1 | 3/2004 | Giannadakis |
| 7,282,055 B2 | 10/2007 | Tsuruta |
| 7,559,934 B2 | 7/2009 | Teague et al. |
| 7,736,356 B2 | 6/2010 | Cooper et al. |
| 7,963,911 B2 | 6/2011 | Turliuc |
| 7,987,046 B1* | 7/2011 | Peterman ............... G01C 21/26 701/454 |
| 8,002,713 B2 | 8/2011 | Heske |
| 8,038,598 B2 | 10/2011 | Khachi |
| 8,092,397 B2 | 1/2012 | Wallace et al. |
| 8,187,173 B2 | 5/2012 | Miyoshi |
| 8,257,303 B2 | 9/2012 | Moll et al. |
| 8,480,595 B2 | 7/2013 | Speeg |
| 8,523,762 B2 | 9/2013 | Miyamoto et al. |
| 8,540,748 B2 | 9/2013 | Murphy et al. |
| 8,820,603 B2 | 9/2014 | Shelton et al. |
| 8,882,660 B2 | 11/2014 | Phee et al. |
| 8,945,163 B2 | 2/2015 | Voegele et al. |
| 8,956,280 B2 | 2/2015 | Eversull et al. |
| 9,345,456 B2 | 5/2016 | Tsonton et al. |
| 9,460,536 B2 | 10/2016 | Hasegawa et al. |
| 9,504,604 B2 | 11/2016 | Alvarez |
| 9,561,083 B2 | 2/2017 | Yu et al. |
| 9,592,042 B2 | 3/2017 | Titus |
| 9,597,152 B2 | 3/2017 | Schaeffer |
| 9,622,827 B2 | 4/2017 | Yu et al. |
| 9,636,184 B2 | 5/2017 | Lee et al. |
| 9,713,509 B2 | 7/2017 | Schuh et al. |
| 9,727,963 B2 | 8/2017 | Mintz et al. |
| 9,730,757 B2 | 8/2017 | Brudniok |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,818,681 B2 | 11/2017 | Machida |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 10,016,900 B1 | 7/2018 | Meyer et al. |
| 10,022,192 B1 | 7/2018 | Ummalaneni |
| 10,145,747 B1 | 12/2018 | Lin et al. |
| 10,159,532 B1 | 12/2018 | Ummalaneni et al. |
| 10,524,866 B2 | 1/2020 | Srinivasan |
| 2002/0019644 A1 | 2/2002 | Hastings |
| 2002/0111608 A1 | 8/2002 | Baerveldt |

(56) References Cited

U.S. PATENT DOCUMENTS

| | | |
|---|---|---|
| 2002/0111621 A1 | 8/2002 | Wallace et al. |
| 2003/0004455 A1 | 1/2003 | Kadziauskas |
| 2003/0040681 A1 | 2/2003 | Ng et al. |
| 2003/0065358 A1 | 4/2003 | Frecker |
| 2003/0109877 A1 | 6/2003 | Morley |
| 2003/0109889 A1 | 6/2003 | Mercereau |
| 2003/0158545 A1 | 8/2003 | Hovda et al. |
| 2003/0208189 A1 | 11/2003 | Payman |
| 2004/0143253 A1 | 7/2004 | Vanney |
| 2004/0153093 A1 | 8/2004 | Donovan |
| 2004/0158261 A1 | 8/2004 | Vu |
| 2004/0186349 A1 | 9/2004 | Ewers |
| 2004/0193146 A1 | 9/2004 | Lee et al. |
| 2004/0210116 A1 | 10/2004 | Nakao |
| 2004/0253079 A1 | 12/2004 | Sanchez |
| 2005/0033270 A1 | 2/2005 | Ramans et al. |
| 2005/0054900 A1 | 3/2005 | Mawn |
| 2005/0159645 A1 | 7/2005 | Bertolero |
| 2005/0240178 A1 | 10/2005 | Morley et al. |
| 2005/0261705 A1 | 11/2005 | Gist |
| 2006/0015133 A1 | 1/2006 | Grayzel |
| 2006/0058813 A1 | 3/2006 | Teague |
| 2006/0116693 A1 | 6/2006 | Weisenburgh |
| 2006/0135963 A1 | 6/2006 | Kick |
| 2006/0156875 A1 | 7/2006 | McRury et al. |
| 2006/0189891 A1 | 8/2006 | Waxman et al. |
| 2007/0016164 A1 | 1/2007 | Dudney et al. |
| 2007/0027443 A1 | 2/2007 | Rose |
| 2007/0027534 A1 | 2/2007 | Bergheim |
| 2007/0032906 A1 | 2/2007 | Sutherland et al. |
| 2007/0106304 A1 | 5/2007 | Hammack |
| 2007/0135803 A1 | 6/2007 | Belson |
| 2007/0208375 A1 | 9/2007 | Nishizawa |
| 2007/0213668 A1 | 9/2007 | Spitz |
| 2007/0239178 A1 | 10/2007 | Weitzner et al. |
| 2007/0250111 A1 | 10/2007 | Lu |
| 2007/0299427 A1 | 12/2007 | Yeung et al. |
| 2008/0015566 A1 | 1/2008 | Livneh |
| 2008/0021440 A1 | 1/2008 | Solomon |
| 2008/0033467 A1 | 2/2008 | Miyamoto et al. |
| 2008/0046122 A1 | 2/2008 | Manzo et al. |
| 2008/0065111 A1 | 3/2008 | Blumenkranz |
| 2008/0125698 A1 | 5/2008 | Greg et al. |
| 2008/0187101 A1 | 8/2008 | Gertner |
| 2008/0196533 A1 | 8/2008 | Bergamasco |
| 2008/0228104 A1 | 9/2008 | Uber et al. |
| 2009/0012507 A1 | 1/2009 | Culbertson et al. |
| 2009/0030446 A1 | 1/2009 | Measamer |
| 2009/0036900 A1 | 2/2009 | Moll |
| 2009/0043305 A1 | 2/2009 | Brodbeck |
| 2009/0082634 A1 | 3/2009 | Kathrani et al. |
| 2009/0088774 A1 | 4/2009 | Swarup et al. |
| 2009/0105723 A1 | 4/2009 | Dillinger |
| 2009/0131885 A1 | 5/2009 | Akahoshi |
| 2009/0161827 A1 | 6/2009 | Gertner et al. |
| 2009/0227998 A1 | 9/2009 | Aljuri |
| 2009/0248041 A1 | 10/2009 | Williams et al. |
| 2009/0248043 A1 | 10/2009 | Tierney et al. |
| 2009/0264878 A1 | 10/2009 | Carmel et al. |
| 2009/0270760 A1 | 10/2009 | Leimbach et al. |
| 2009/0287188 A1 | 11/2009 | Golden et al. |
| 2009/0299352 A1 | 12/2009 | Zerfas |
| 2010/0004642 A1 | 1/2010 | Lumpkin |
| 2010/0010504 A1 | 1/2010 | Simaan et al. |
| 2010/0011900 A1 | 1/2010 | Burbank |
| 2010/0011901 A1 | 1/2010 | Burbank |
| 2010/0082017 A1 | 4/2010 | Zickler |
| 2010/0179632 A1 | 7/2010 | Bruszewski et al. |
| 2010/0204605 A1 | 8/2010 | Blakley |
| 2010/0204646 A1 | 8/2010 | Plicchi et al. |
| 2010/0217235 A1 | 8/2010 | Thorstenson |
| 2010/0225209 A1 | 9/2010 | Goldberg |
| 2010/0228249 A1 | 9/2010 | Mohr |
| 2010/0268211 A1 | 10/2010 | Manwaring et al. |
| 2010/0312141 A1 | 12/2010 | Keast et al. |
| 2010/0331858 A1 | 12/2010 | Simaan et al. |
| 2011/0015483 A1 | 1/2011 | Barbagli |
| 2011/0071541 A1 | 3/2011 | Prisco et al. |
| 2011/0071543 A1 | 3/2011 | Prisco et al. |
| 2011/0106146 A1 | 5/2011 | Jeong |
| 2011/0125165 A1 | 5/2011 | Simaan et al. |
| 2011/0152880 A1 | 6/2011 | Alvarez et al. |
| 2011/0160713 A1 | 6/2011 | Neuberger |
| 2011/0167611 A1 | 7/2011 | Williams |
| 2011/0213362 A1 | 9/2011 | Cunningham |
| 2011/0224660 A1 | 9/2011 | Neuberger et al. |
| 2011/0238064 A1 | 9/2011 | Williams et al. |
| 2011/0257641 A1 | 10/2011 | Hastings et al. |
| 2011/0276085 A1 | 11/2011 | Krzyzanowski |
| 2011/0313343 A1 | 12/2011 | Milutinovic et al. |
| 2012/0069167 A1 | 3/2012 | Liu et al. |
| 2012/0253277 A1 | 4/2012 | Tah et al. |
| 2012/0138586 A1 | 6/2012 | Webster et al. |
| 2012/0209315 A1 | 8/2012 | Amat |
| 2012/0232342 A1 | 9/2012 | Reydel |
| 2012/0253332 A1 | 10/2012 | Moll |
| 2012/0259320 A1 | 10/2012 | Loesel et al. |
| 2012/0296318 A1 | 11/2012 | Wellhofer et al. |
| 2013/0006144 A1 | 1/2013 | Clancy |
| 2013/0035537 A1 | 2/2013 | Wallace et al. |
| 2013/0053877 A1 | 2/2013 | BenMaamer |
| 2013/0066136 A1 | 3/2013 | Palese et al. |
| 2013/0085442 A1 | 4/2013 | Shtul et al. |
| 2013/0085486 A1 | 4/2013 | Boutoussov et al. |
| 2013/0096422 A1 | 4/2013 | Boctor |
| 2013/0096574 A1 | 4/2013 | Kang et al. |
| 2013/0110042 A1 | 5/2013 | Humphreys |
| 2013/0110107 A1 | 5/2013 | Smith et al. |
| 2013/0116716 A1 | 5/2013 | Bahls et al. |
| 2013/0144274 A1 | 6/2013 | Stefanchik et al. |
| 2013/0144395 A1 | 6/2013 | Stefanchik |
| 2013/0190796 A1 | 7/2013 | Tilson et al. |
| 2013/0225997 A1 | 8/2013 | Dillard et al. |
| 2013/0226161 A1 | 8/2013 | Hickenbotham |
| 2013/0253267 A1 | 9/2013 | Collins |
| 2013/0303876 A1 | 11/2013 | Gelfand et al. |
| 2013/0310819 A1 | 11/2013 | Neuberger et al. |
| 2013/0345686 A1 | 12/2013 | Brown |
| 2014/0005681 A1 | 1/2014 | Gee et al. |
| 2014/0039681 A1 | 2/2014 | Bowling |
| 2014/0046308 A1 | 2/2014 | Bischoff |
| 2014/0051985 A1 | 2/2014 | Fan |
| 2014/0058365 A1 | 2/2014 | Bille |
| 2014/0058404 A1 | 2/2014 | Hammack |
| 2014/0058428 A1 | 2/2014 | Christopher |
| 2014/0100445 A1 | 4/2014 | Stenzel |
| 2014/0142591 A1 | 5/2014 | Alvarez et al. |
| 2014/0163318 A1 | 6/2014 | Swanstrom |
| 2014/0194859 A1 | 7/2014 | Ianchulev |
| 2014/0194905 A1 | 7/2014 | Kappel |
| 2014/0243849 A1 | 8/2014 | Saglam |
| 2014/0275956 A1 | 9/2014 | Fan |
| 2014/0276723 A1 | 9/2014 | Parihar |
| 2014/0276956 A1 | 9/2014 | Crainich |
| 2014/0309649 A1 | 10/2014 | Alvarez et al. |
| 2014/0309655 A1 | 10/2014 | Gal et al. |
| 2014/0316203 A1 | 10/2014 | Carroux et al. |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0051592 A1 | 2/2015 | Kintz |
| 2015/0080879 A1 | 3/2015 | Trees |
| 2015/0101442 A1 | 4/2015 | Romo |
| 2015/0119638 A1 | 4/2015 | Yu et al. |
| 2015/0127045 A1 | 5/2015 | Prestel |
| 2015/0133960 A1 | 5/2015 | Lohmeier |
| 2015/0164522 A1 | 6/2015 | Budiman |
| 2015/0164594 A1 | 6/2015 | Romo et al. |
| 2015/0164596 A1 | 6/2015 | Romo |
| 2015/0201917 A1 | 7/2015 | Snow |
| 2015/0202085 A1 | 7/2015 | Lemonis |
| 2015/0314110 A1 | 11/2015 | Park |
| 2015/0335480 A1 | 11/2015 | Alvarez et al. |
| 2016/0001038 A1 | 1/2016 | Romo et al. |

(56) References Cited

U.S. PATENT DOCUMENTS

| | | |
|---|---|---|
| 2016/0022289 A1 | 1/2016 | Wan |
| 2016/0022466 A1 | 1/2016 | Pedtke |
| 2016/0030073 A1 | 2/2016 | Lsakov |
| 2016/0045208 A1 | 2/2016 | Ciulla |
| 2016/0051318 A1 | 2/2016 | Manzo et al. |
| 2016/0066935 A1 | 3/2016 | Nguyen et al. |
| 2016/0158490 A1 | 6/2016 | Leeflang |
| 2016/0183841 A1 | 6/2016 | Duindam et al. |
| 2016/0199984 A1 | 7/2016 | Lohmeier et al. |
| 2016/0235495 A1 | 8/2016 | Wallace et al. |
| 2016/0249932 A1 | 9/2016 | Rogers et al. |
| 2016/0270865 A1 | 9/2016 | Landey et al. |
| 2016/0279394 A1 | 9/2016 | Moll et al. |
| 2016/0287279 A1 | 10/2016 | Bovay et al. |
| 2016/0296294 A1 | 10/2016 | Moll et al. |
| 2016/0303743 A1 | 10/2016 | Rockrohr |
| 2016/0331358 A1 | 11/2016 | Gordon |
| 2016/0367324 A1 | 12/2016 | Sato et al. |
| 2016/0374541 A1 | 12/2016 | Agrawal et al. |
| 2017/0007337 A1 | 1/2017 | Dan |
| 2017/0049471 A1 | 2/2017 | Gaffney et al. |
| 2017/0065227 A1 | 3/2017 | Marrs |
| 2017/0065364 A1 | 3/2017 | Schuh et al. |
| 2017/0065365 A1* | 3/2017 | Schuh .................. A61B 34/70 |
| 2017/0095234 A1 | 4/2017 | Prisco et al. |
| 2017/0095295 A1 | 4/2017 | Overmyer |
| 2017/0100199 A1 | 4/2017 | Yu et al. |
| 2017/0119411 A1 | 5/2017 | Shah |
| 2017/0119412 A1 | 5/2017 | Noonan et al. |
| 2017/0119413 A1 | 5/2017 | Romo |
| 2017/0119481 A1 | 5/2017 | Romo et al. |
| 2017/0135706 A1 | 5/2017 | Frey |
| 2017/0151416 A1* | 6/2017 | Kutikov ............ A61M 5/14216 |
| 2017/0165011 A1 | 6/2017 | Bovay et al. |
| 2017/0172553 A1 | 6/2017 | Chaplin |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0252096 A1 | 9/2017 | Felder |
| 2017/0265923 A1 | 9/2017 | Privitera |
| 2017/0290631 A1 | 10/2017 | Lee et al. |
| 2017/0319289 A1 | 11/2017 | Neff et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0000563 A1* | 1/2018 | Shanjani ............... A61B 5/0015 |
| 2018/0025666 A1 | 1/2018 | Ho et al. |
| 2018/0049824 A1* | 2/2018 | Harris .................. A61B 34/30 |
| 2018/0055583 A1 | 3/2018 | Schuh et al. |
| 2018/0177383 A1 | 6/2018 | Noonan et al. |
| 2018/0177556 A1 | 6/2018 | Noonan |
| 2018/0177561 A1 | 6/2018 | Mintz et al. |
| 2018/0193049 A1 | 7/2018 | Heck et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0296285 A1 | 10/2018 | Simi et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0099231 A1 | 4/2019 | Bruehwiler |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0228528 A1 | 7/2019 | Mintz et al. |
| 2019/0239890 A1 | 8/2019 | Stokes |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0314616 A1 | 10/2019 | Moll et al. |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0039086 A1 | 2/2020 | Meyer |
| 2020/0046434 A1 | 2/2020 | Graetzel |
| 2020/0054405 A1 | 2/2020 | Schuh |
| 2020/0054408 A1 | 2/2020 | Schuh et al. |
| 2020/0060516 A1 | 2/2020 | Baez |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |

FOREIGN PATENT DOCUMENTS

| | | |
|---|---|---|
| JP | 2005-270464 | 10/2005 |
| WO | WO 11/161218 | 12/2011 |
| WO | WO 13/107468 | 7/2013 |
| WO | WO 13/130895 | 9/2013 |
| WO | WO 16/137612 | 9/2016 |
| WO | WO 17/114855 | 7/2017 |
| WO | WO 18/069679 | 4/2018 |

OTHER PUBLICATIONS

Extended European Search Report dated Oct. 28, 2020 in patent application No. 18780953.8.

\* cited by examiner

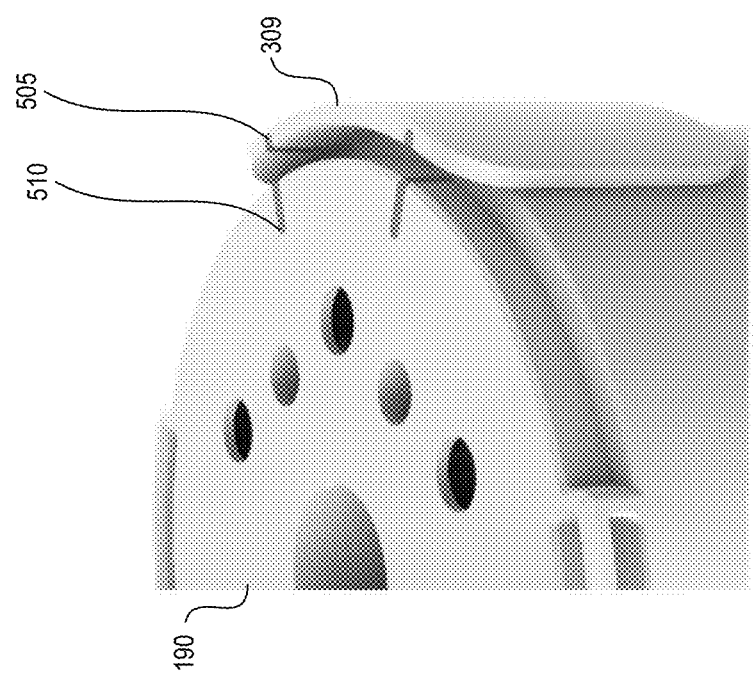
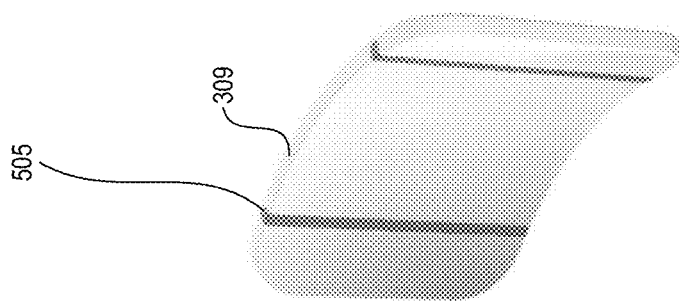
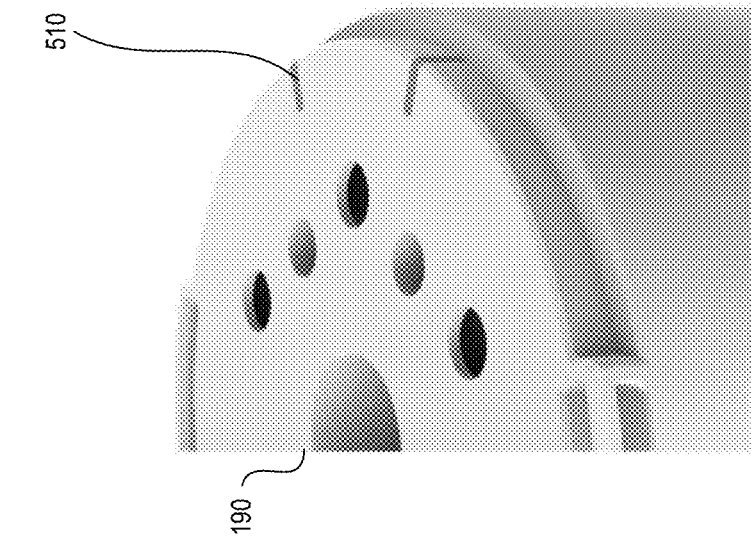
FIG. 5B
FIG. 5A

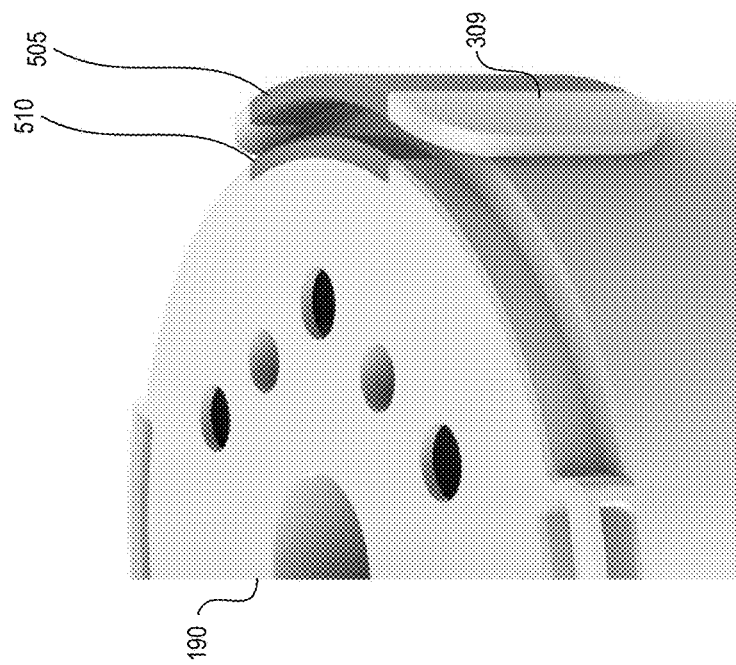
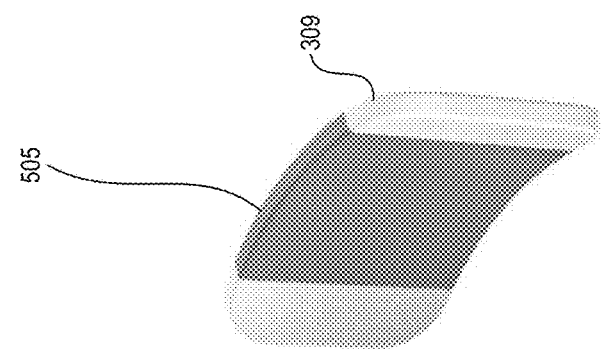
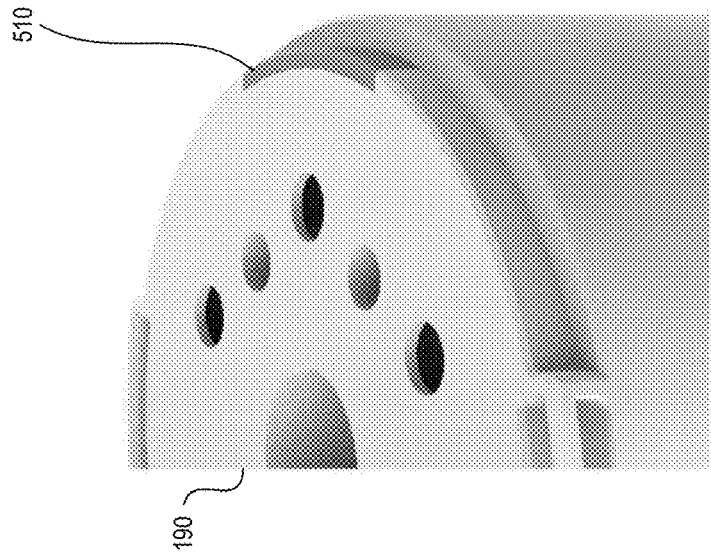
FIG. 5F
FIG. 5E

PATIENT INTRODUCER ALIGNMENT

CROSS-REFERENCE TO RELATED APPLICATION

This application claims the benefit of U.S. Provisional Application No. 62/483,279, filed Apr. 7, 2017, which is hereby incorporated by reference in its entirety.

TECHNICAL FIELD

The present disclosure relates generally to an alignment device, and more particularly to a patient introducer including an alignment member for aligning the patient introducer with a manipulator assembly of a robotic system.

BACKGROUND

Medical procedures such as endoscopy (e.g., bronchoscopy) may involve accessing and visualizing the inside of a patient's luminal network (e.g., airways) for diagnostic and/or therapeutic purposes. Surgical robotic systems may be used to control the insertion and/or manipulation of a surgical tool, such as, for example, an endoscope during an endoscopic procedure. The surgical robotic system may comprise at least one robotic arm including a manipulator assembly used to control the positioning of the surgical tool during the procedure. The surgical tool may be introduced into the patient's luminal network via a patient introducer which may receive and guide the surgical tool from the manipulator assembly into the patient's luminal network.

SUMMARY

The systems, methods and devices of this disclosure each have several innovative aspects, no single one of which is solely responsible for the desirable attributes disclosed herein.

In one aspect, there is provided a patient introducer, including an introducer tube extending between (i) a distal end connectable to a port and (ii) a proximal end configured to receive a surgical tool, the introducer tube configured to guide the surgical tool into the port; and an alignment member connected to the introducer tube and comprising a first shape and a first alignment marking, the alignment member configured to interface with a manipulator assembly of a robotic system. The manipulator assembly may include a second shape and a second alignment marking, the first shape being complementary to the second shape, wherein the first alignment marking of the alignment member facilitates rotational alignment of the alignment member and the manipulator assembly.

In another aspect, there is provided method of positioning a patient introducer and a robotic arm of a surgical robotic system. The method may involve aligning a patient introducer to a port, the patient introducer including: an introducer tube extending between (i) a distal end connectable to the port and (ii) a proximal end configured to receive a surgical tool from the robotic arm, the introducer tube configured to guide the surgical tool into the port, and an alignment member connected to the introducer tube and including a first shape and a first alignment marking. The method may also involve placing the robotic arm into an alignment position, a manipulator assembly being connected to a distal portion of the robotic arm, the manipulator assembly including a second shape and a second alignment marking, the second shape being complementary to the first shape. The method may further involve rotationally aligning the manipulator assembly and the alignment member based on aligning the second alignment marking of the manipulator assembly with the first alignment marking of the alignment member.

In yet another aspect, there is provided a patient introducer including an introducer tube configured to receive a surgical tool and guide the surgical tool into a patient; and an alignment member connected to the introducer tube, the alignment member configured to interface with a manipulator assembly of a surgical robotic system and facilitate rotational alignment with the manipulator assembly.

In still yet another aspect, there is provided surgical robotic system, including a robotic arm; and a manipulator assembly attached to a distal portion of the robotic arm, the manipulator assembly configured to control a surgical tool for insertion into a patient introducer. The manipulator assembly may be configured to interface with an alignment member of the patient introducer and facilitate rotational alignment with the patient introducer.

BRIEF DESCRIPTION OF THE DRAWINGS

The disclosed aspects will hereinafter be described in conjunction with the appended drawings and appendices, provided to illustrate and not to limit the disclosed aspects, wherein like designations denote like elements.

FIGS. 5A-5H illustrate embodiments of alignment markings which may be used to aid in rotational alignment of a manipulator assembly with an alignment member in accordance with aspects of this disclosure.

DETAILED DESCRIPTION

Figure 1A:
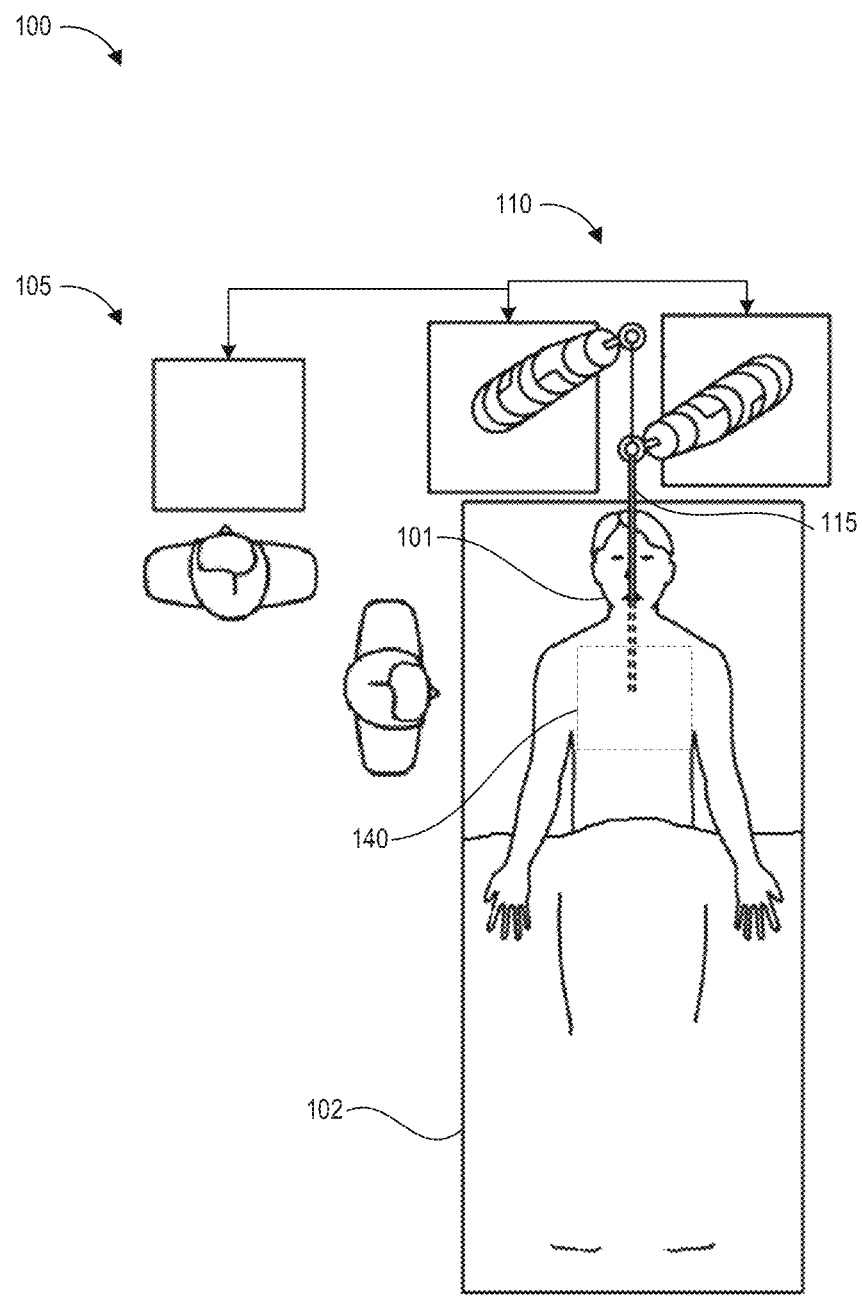
FIG. 1A illustrates an example operating environment including an example surgical robotic system in accordance with aspects of this disclosure.

Embodiments of this disclosure relate to systems and techniques that facilitate the alignment of a patient introducer with a surgical robotic system. A patient introducer may function as a guide for a surgical tool (e.g., an endoscopic tool) and may guide the surgical tool into a port (e.g., an endotracheal tube) to introduce the endoscopic tool into a patient. As used herein, a "port" may refer to a device partially insertable into of a lumen of a patient, that is configured to guide a surgical tool into a surgical site. Additional examples of ports include but are not limited to endotracheal tubes, gastrointestinal tubes, cannulas, cystoscopy sheaths, and the like. Certain embodiments of the patient introducer may guide the surgical tool along a curved path, where the entry and exit points of the patient introducer are formed along the curved path, rather than along a straight line. This curvature of the patient introducer enables arms of a surgical robot to be positioned outside of a straight line extending from the port, providing for more practical and/or convenient placement of a surgical robotic system cart to which the robotic arms are attached. That is, without the curved entry provided by the patient introducer, it may be necessary for the arms of the surgical robotic system to be substantially aligned with an axis of the port for proper control the surgical tool, which may not be practical under certain circumstances.

As used herein, the term "approximately" refers to a range of measurements of a length, thickness, a quantity, time period, or other measurable value. Such range of measurements encompasses variations of +/−10% or less, preferably +/−5% or less, more preferably +/−1% or less, and still more preferably +/−0.1% or less, of and from the specified value, in so far as such variations are appropriate in order to function in the disclosed devices, systems, and techniques.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

Overview of Example Surgical Robotic Systems

The embodiments discussed herein, although described in connection with a bronchoscopy embodiment, may also cover other types of medical or surgical procedures that may be performed by a surgical robotic system, such as cardiology, urology, gastroenterology, laparoscopy, and/or other related or similar surgical procedures including surgical procedures in which a surgical tool is introduced into a patient's body via, for example, a port installed on and/or partially inserted into the patient's body.

FIG. 1A illustrates an example operating environment implementing one or more aspects of the disclosed surgical robotic systems and techniques. The operating environment 100 includes a patient 101, a platform 102 (also referred to as a table or bed) supporting the patient 101, a surgical robotic system 110 (also referred to simply as a robotic system) guiding movement of a surgical tool 115 (e.g., an endoscopic tool, also referred to simply as an endoscope 115), and a command center 105 for controlling operations of the surgical robotic system 110. FIG. 1A also illustrates an outline of a region of a luminal network 140 within the patient 101, shown in more detail in FIG. 1B.

The surgical robotic system 110 can include one or more robotic arms for positioning and guiding movement of the endoscope 115 through the luminal network 140 of the patient 101. Command center 105 can be communicatively coupled to the surgical robotic system 110 for receiving position data and/or providing control signals from a user. As used herein, "communicatively coupled" refers to any wired and/or wireless data transfer mediums, including but not limited to a wireless wide area network (WWAN) (e.g., one or more cellular networks), a wireless local area network (WLAN) (e.g., configured for one or more standards, such as the IEEE 802.11 (Wi-Fi)), Bluetooth, data transfer cables, and/or the like. The surgical robotic system 110 is discussed in more detail with respect to FIG. 1C, and the command center 105 is discussed in more detail with respect to FIG. 2.

The endoscope 115 may be, for example, a tubular and flexible surgical instrument that, in use, is inserted into the anatomy of a patient to capture images of the anatomy (e.g., body tissue) and provide a working channel for insertion of other medical instruments to a target tissue site. In some implementations, the endoscope 115 can be a bronchoscope. The endoscope 115 can include one or more imaging devices (e.g., cameras or other types of optical sensors) at its distal end. The imaging devices may include one or more optical components such as an optical fiber, fiber array, photosensitive substrate, and/or lens(es). The optical components move along with the tip of the endoscope 115 such that movement of the tip of the endoscope 115 results in corresponding changes to the field of view of the images captured by the imaging devices.

Figure 1B:
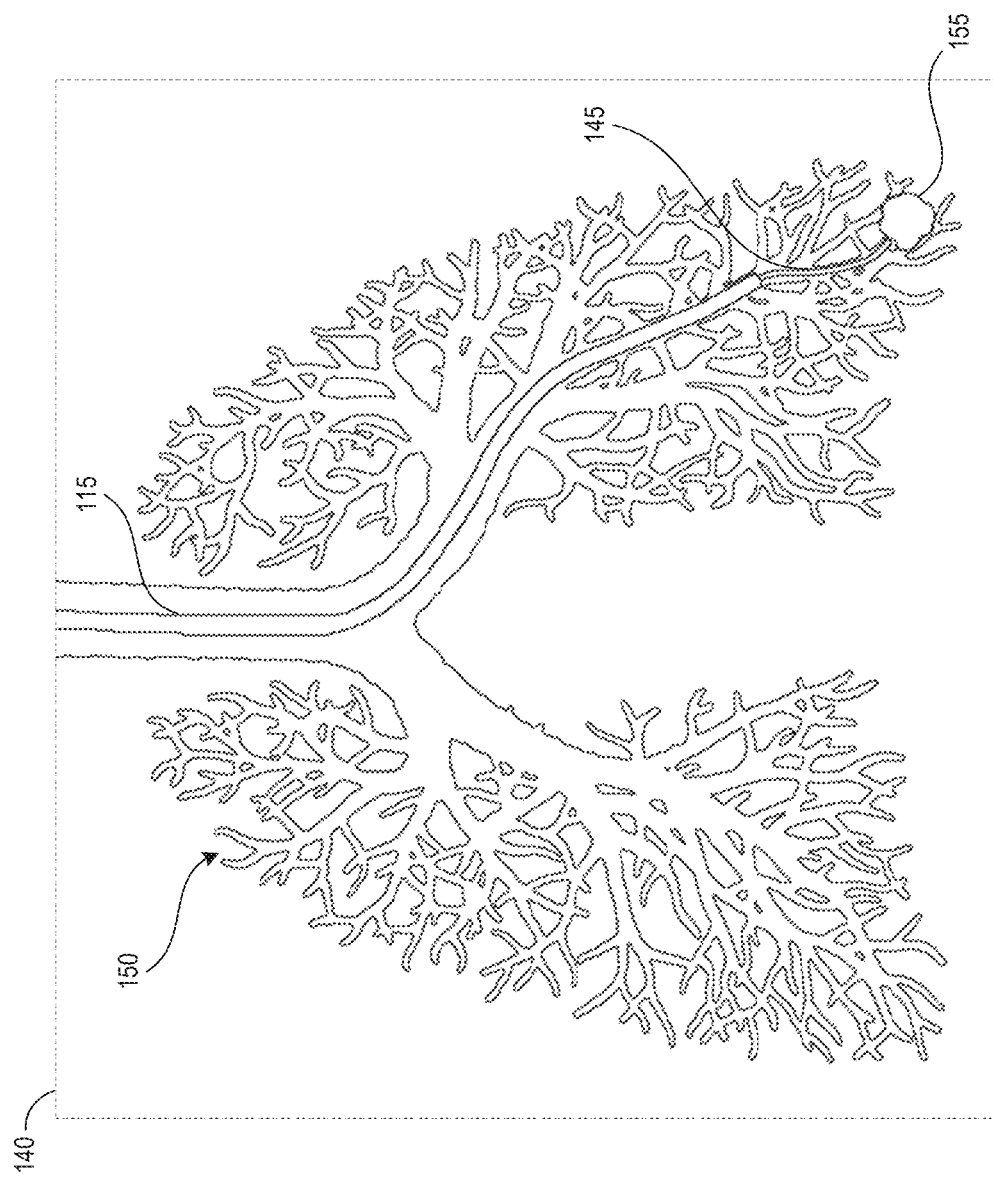
FIG. 1B illustrates an example luminal network that can be navigated in the operating environment of FIG. 1A.

FIG. 1B illustrates an example luminal network that can be navigated in the operating environment of FIG. 1A. The luminal network 140 includes the branched structure of the airways 150 of the patient 101 and a lesion 155 that can be accessed as described herein for diagnosis and/or treatment. As illustrated, the lesion 155 is located at the periphery of the airways 150. The endoscope 115 has a first diameter and thus its distal end is not able to be positioned through the smaller-diameter airways around the lesion 155. Accordingly, a steerable catheter 145 extends from the working channel of the endoscope 115 the remaining distance to the lesion 155. The steerable catheter 145 may have a lumen through which instruments, for example biopsy needles, cytology brushes, and/or tissue sampling forceps, can be passed to the target tissue site of lesion 155. In such implementations, both the distal end of the endoscope 115 and the distal end of the steerable catheter 145 can be provided with electro-magnetic (EM) sensors for tracking their position within the airways 150. In other embodiments, the overall diameter of the endoscope 115 may be small enough to reach the periphery without the steerable catheter 155, or may be small enough to get close to the periphery (e.g., within 2.5-3 cm) to deploy medical instruments through a non-steerable catheter.

In some embodiments, a 2D display of a 3D luminal network model as described herein, or a cross-section of a 3D model, can resemble FIG. 1B.

Figure 1C:
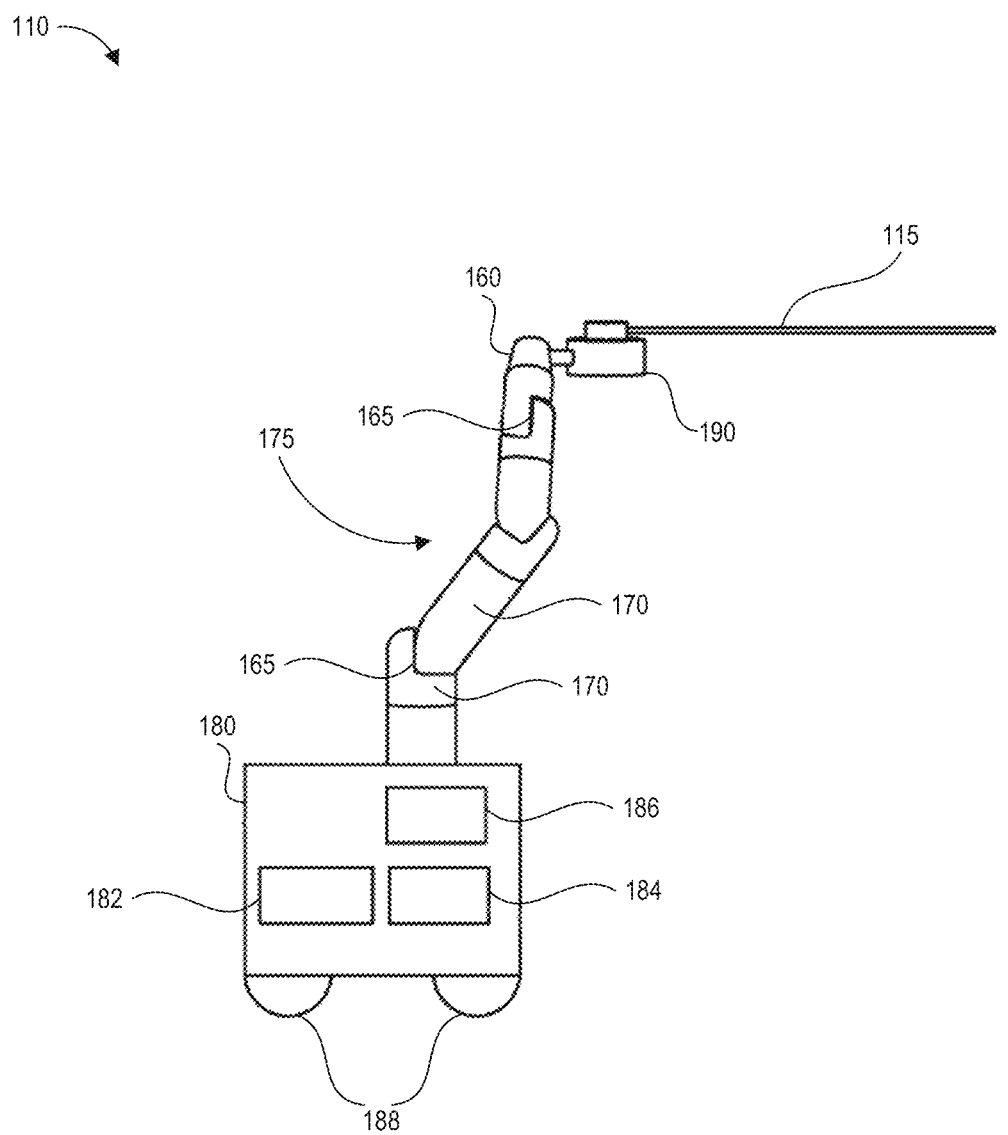
FIG. 1C illustrates an example robotic arm of a robotic surgical system for guiding surgical tool movement through the luminal network of FIG. 1B.

FIG. 1C illustrates an example robotic arm of a surgical robotic system for guiding surgical tool movement through the luminal network of FIG. 1B. The surgical robotic system 110 may include, for example, a surgical robotic system cart 180 (also referred to simply as a cart or a base) coupled to one or more robotic arms, e.g., robotic arm 175 (also referred to simply as an arm). Although the embodiments discussed herein are described with respect to the specific embodiment of a cart approach (e.g., the robotic arms 175 are positioned on the surgical robotic system cart 180), other embodiments of this disclosure may also relate to other approaches, such as, for example, a table approach in which the patient 101 lies on a table (e.g., the platform 102) and the robotic arms 175 are also attached to the table. The robotic arm 175 includes multiple arm segments 170 coupled at joints 165, which provides the robotic arm 175 multiple degrees of freedom. As an example, one implementation of the robotic arm 175 can have seven degrees of freedom corresponding to seven arm segments. In some embodiments, the robotic arm 175 includes set up joints that use a combination of brakes and counter-balances to maintain a position of the robotic arm 175. The counter-balances may include gas springs or coil springs. The brakes, e.g., fail safe brakes, may be include mechanical and/or electrical components. Further, the robotic arm 175 may be gravity-assisted passive support type robotic arm.

The robotic arm 175 may be coupled to a manipulator assembly (e.g., an instrument device manipulator (IDM) 190) using a mechanism changer interface (MCI) 160. As used herein, a "manipulator assembly" may refer to an IDM 190 and any other instruments connected or integrated with the IDM 190. For example, a sterile adaptor may be connected to the IDM 190 for certain surgical procedures where sterility is necessary for the manipulator assembly. The sterile adaptor may be part of, for example, a sterile drape that covers one or more sterile component(s) of a surgical robotic system and may facilitate maintaining a sterile interface between the IDM 190 and one or more components of the robotic arm 175 or surgical tool 115, thereby providing a barrier between non-sterile component(s) of the robotic system and a sterile surgical zone or area. The sterile adaptor may cover certain markings on the IDM 190, and thus, in some embodiments, the sterile adaptor may include markings formed thereon. The markings on the sterile adaptor may be located in positions that correspond to the markings on the IDM 190. The IDM 190 can be removed and replaced with a different type of IDM, for example, a first type of IDM configured to manipulate an endoscope or a second type of IDM configured to manipulate a laparoscope. The MCI 160 includes connectors to transfer pneumatic pressure, electrical power, electrical signals, and/or optical signals from the robotic arm 175 to the IDM 190. The MCI 160 can be a set screw or base plate connector. The IDM 190 can manipulate surgical tools or instruments, for example the endo scope 115, using techniques including direct drive, harmonic drive, geared drives, belts and pulleys, magnetic drives, and the like. In certain implementations, the MCI 160 is interchangeable based on the type of IDM 190 and can be customized for a certain type of surgical procedure. The robotic 175 arm can include a joint level torque sensing and a wrist at a distal end.

Robotic arm 175 of the surgical robotic system 110 can manipulate the endoscope 115 using elongate movement members. The elongate movement members may include pull wires, also referred to as pull or push wires, cables, fibers, or flexible shafts. For example, the robotic arm 175 can actuate multiple pull wires coupled to the endoscope 115 to deflect the tip of the endoscope 115. The pull wires may include both metallic and non-metallic materials, for example, stainless steel, Kevlar, tungsten, carbon fiber, and/or the like. The endoscope 115 may exhibit nonlinear behavior in response to forces applied by the elongate movement members. The nonlinear behavior may be based on stiffness and compressibility of the endoscope 115, as well as variability in slack or stiffness between different elongate movement members.

The base 180 can be positioned such that the robotic arm 175 has access to perform or assist with a surgical procedure on a patient, while a user such as a physician may control the surgical robotic system 110 from the comfort of the command console 105. In some embodiments, the base 180 may be coupled to a surgical operating table or bed for supporting the patient 101. The base 180 can be communicatively coupled to the command console 105 shown in FIG. 1A.

The base 180 can include a source of power 182, pneumatic pressure 186, and control and sensor electronics 184—including components such as, e.g., a central processing unit (also referred to simply as a processor), data bus, control circuitry, and/or memory—and related actuators such as motors to move the robotic arm 175. The electronics 184 can implement navigation control techniques, safety modes, and/or data filtering techniques. The electronics 184 in the base 180 may also process and transmit control signals communicated from the command console 105. In some embodiments, the base 180 includes wheels 188 to transport the surgical robotic system 110 and wheel locks/brakes (not shown) for the wheels 188. Mobility of the surgical robotic system 110 helps accommodate space constraints in a surgical operating room as well as facilitate appropriate positioning and movement of surgical equipment in order to align the base 180 and/or IDM 190 with the patient. Further, the mobility allows the robotic arm 175 to be aligned with the patient 101 and/or the platform 102 such that the robotic arm 175 does not interfere with the patient, physician, anesthesiologist, or any other equipment during procedures. A user may control the robotic arm 175 using control devices, for example the command console in order to perform various procedures.

Figure 2:
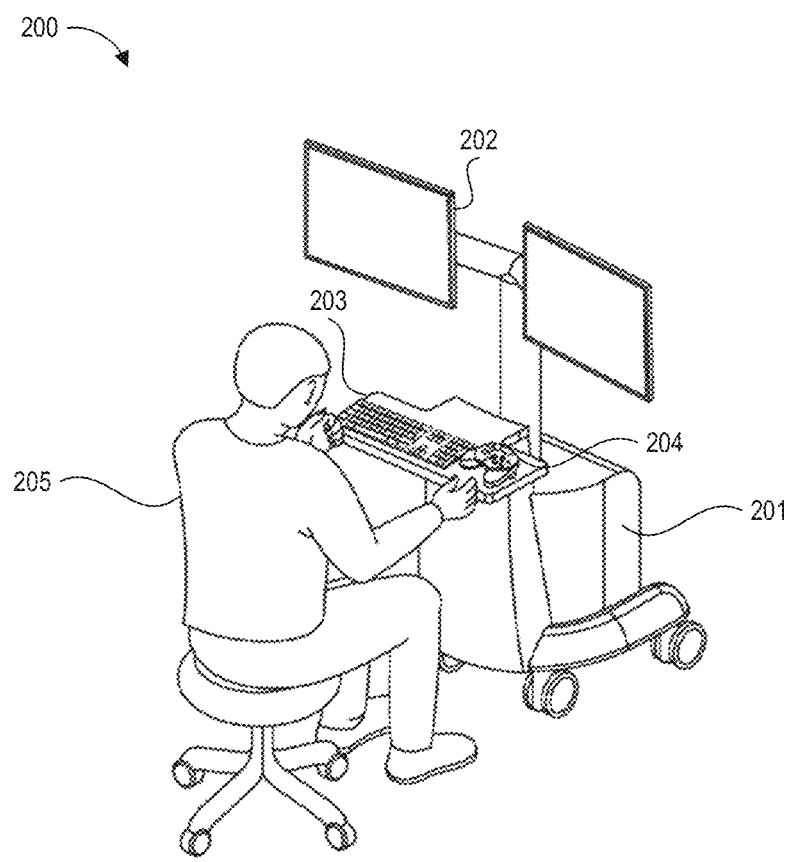
FIG. 2 illustrates an example command console that can be used in the example operating environment of FIG. 1A.

FIG. 2 illustrates an example command console 200 that can be used, for example, as the command console 105 in the example operating environment 100. The command console 200 includes a console base 201, display modules 202, e.g., monitors, and control modules or input devices, e.g., a keyboard 203 and/or a joystick 204. In some embodiments, one or more of the command console 200 functionality may be integrated into a base 180 of the surgical robotic system 110 or another system communicatively coupled to the surgical robotic system 110. A user 205, e.g., a physician, may remotely control the surgical robotic system 100 from an ergonomic position using the command console 200.

The console base 201 may include a central processing unit, a memory unit, a data bus, and associated data communication ports that are responsible for interpreting and processing signals such as camera imagery and tracking sensor data, e.g., from the endoscope 115 shown in FIGS. 1A-1C. In some embodiments, both the console base 201 and the base 180 perform signal processing for load-balancing. The console base 201 may also process commands and instructions provided by the user 205 through the control modules 203 and 204. In addition to the keyboard 203 and joystick 204 shown in FIG. 2, the control modules may include other devices, for example, computer mice, trackpads, trackballs, control pads, video game controllers, and sensors (e.g., motion sensors or cameras) that capture hand gestures and finger gestures.

In some embodiments, the user 205 can control a surgical instrument such as the endoscope 115 using the command console 200 in a velocity mode or position control mode. In velocity mode, the user 205 directly controls pitch and yaw motion of a distal end of the endoscope 115 based on direct manual control using the control modules. For example, movement on the joystick 204 may be mapped to yaw and pitch movement in the distal end of the endoscope 115. The joystick 204 can provide haptic feedback to the user 205. For example, the joystick 204 may vibrate to indicate that the endoscope 115 cannot further translate or rotate in a certain direction. The command console 200 can also provide visual feedback (e.g., pop-up messages) and/or audio feedback (e.g., beeping or other audible alert) to indicate that the endoscope 115 has reached maximum translation or rotation. The haptic and/or visual feedback can also be provided due to the system operating in a safety mode during patient expiration as described in more detail below.

In position control mode, the command console 200 uses a three-dimensional (3D) map of a patient luminal network and input from navigational sensors as described herein to control a surgical tool or instrument, e.g., the endoscope 115. The command console 200 provides control signals to robotic arms 175 of the surgical robotic system 110 to manipulate the endoscope 115 to a target location. Due to the reliance on the 3D map, position control mode may require accurate mapping of the anatomy of the patient 101.

In some embodiments, users 205 can manually manipulate robotic arms 175 of the surgical robotic system 110 without using the command console 200. For example, the IDM 190, robotic arm, and/or another portion of the surgical robotic system 110 may include an admittance button 410 (shown in the example of FIG. 4B) which the user can push to begin manual control of one or more of the robotic arms 175. In one embodiment, while the user continuously pressed the admittance button 410, a corresponding robotic arm 175 may allow the user 205 to manually position the IDM 190 by applying physical force to the IDM 190 and/or the robotic arm 175. As described above, the robotic arm 175 may include brake(s) and/or counter balances used to maintain the position and/or orientation of the robotic arm 175. In certain embodiments, the admittance button 410, when actuated by a user (e.g., when receiving an input from a user), may at least partially disengage the brake to allow for movement of the robotic arm 175 in response to an external force applied thereto. In some embodiments, the robotic arm 175 may include an actuator configured to apply a torque to the robotic arm 175 to maintain the spatial positioning and orientation of the robotic arm 175. The robotic arm 175 may be configured to reduce the torque applied to the robotic arm 175 by the actuator, in response to the admittance button 410 receiving input from a user, to allow for movement of the robotic arm 175 in response to an external force applied thereto.

During setup in a surgical operating room, the users 205 may move the robotic arms 102, endoscopes 115, and other surgical equipment to access a patient. Setup may also involve a step of aligning portion(s) of the surgical robotic system 110 with the patient 101, the platform 102, and/or a patient introducer, as discussed in detail below. The surgical robotic system 110 may rely on force feedback and inertia control from the users 205 to determine appropriate configuration of the robotic arms 175 and equipment.

The displays 202 may include one or more electronic monitors (e.g., LCD displays, LED displays, touch-sensitive displays), virtual reality viewing devices, e.g., goggles or glasses, and/or other display devices. In some embodiments, the display modules 202 are integrated with the control modules, for example, as a tablet device with a touchscreen. In some embodiments, one of the displays 202 can display a 3D model of the patient's luminal network and virtual navigation information (e.g., a virtual representation of the end of the endoscope within the model based on EM sensor position) while the other of the displays 202 can display image information received from the camera or another sensing device at the end of the endoscope 115. In some implementations, the user 205 can both view data and input commands to the surgical robotic system 110 using the integrated displays 202 and control modules. The displays 202 can display 2D renderings of 3D images and/or 3D images using a stereoscopic device, e.g., a visor or goggles. The 3D images provide an "endo view" (i.e., endoscopic view), which is a computer 3D model illustrating the anatomy of a patient. The "endo view" provides a virtual environment of the patient's interior and an expected location of an endoscope 115 inside the patient. A user 205 compares the "endo view" model to actual images captured by a camera to help mentally orient and confirm that the endoscope 115 is in the correct—or approximately correct—location within the patient. The "endo view" provides information about anatomical structures, e.g., the shape of airways, circulatory vessels, or an intestine or colon of the patient, around the distal end of the endoscope 115. The display modules 202 can simultaneously display the 3D model and CT scans of the anatomy the around distal end of the endoscope 115. Further, the display modules 202 may overlay the already determined navigation paths of the endoscope 115 on the 3D model and/or CT scans.

In some embodiments, a model of the endoscope 115 is displayed with the 3D models to help indicate a status of a surgical procedure. For example, the CT scans identify a lesion in the anatomy where a biopsy may be necessary. During operation, the display modules 202 may show a reference image captured by the endoscope 115 corresponding to the current location of the endoscope 115. The display modules 202 may automatically display different views of the model of the endoscope 115 depending on user settings and a particular surgical procedure. For example, the display modules 202 show an overhead fluoroscopic view of the endoscope 115 during a navigation step as the endoscope 115 approaches an operative region of a patient.

Overview of Patient Introducer Examples

Figure 3A:
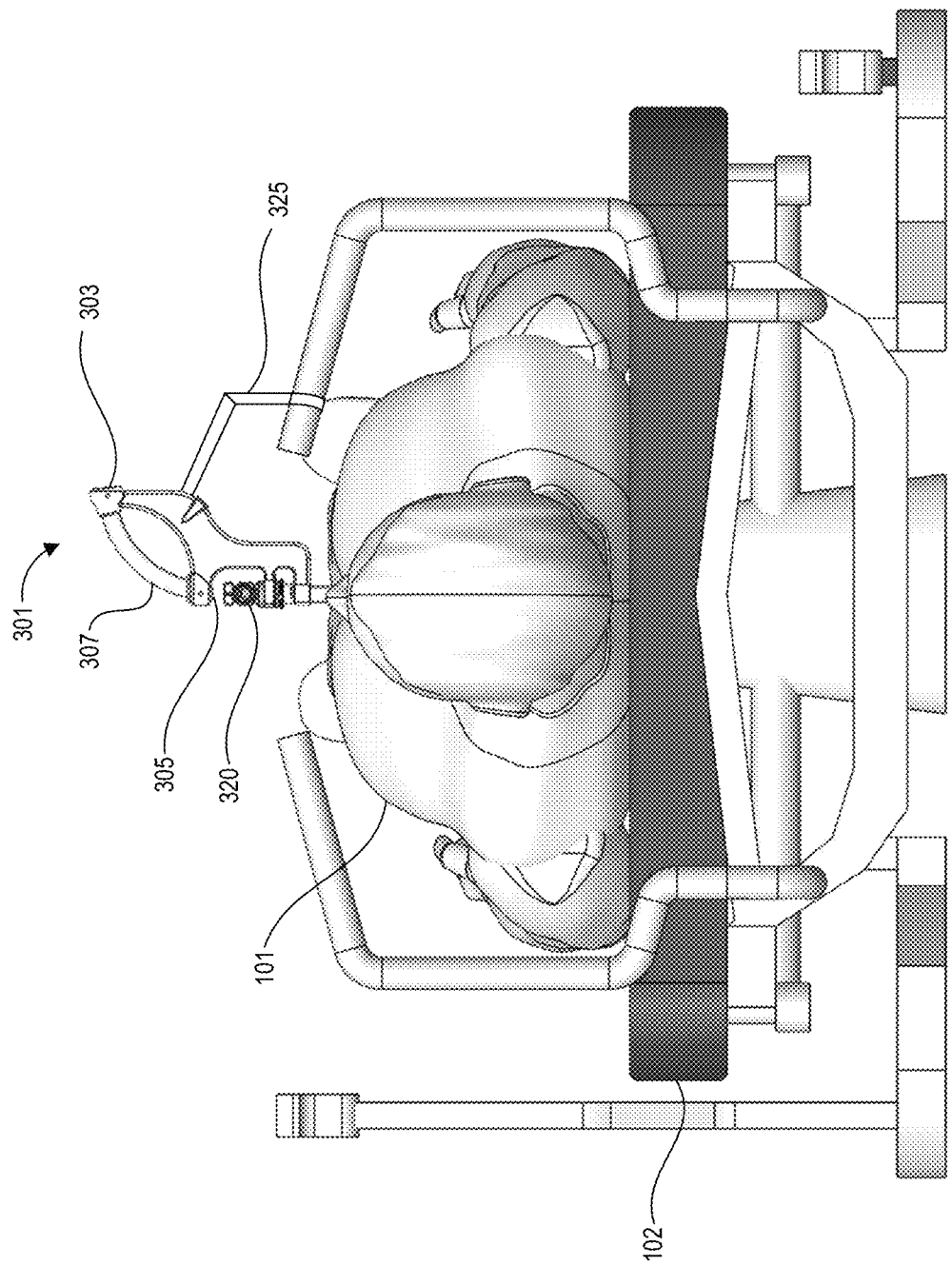
FIG. 3A illustrates an example patient introducer in accordance with one or more aspects of this disclosure.

FIG. 3A illustrates an example patient introducer 301 in accordance with one or more aspects of this disclosure. In the example of FIG. 3A, the patient introducer 301 is attached to a patient 101 via a port 320. In the embodiment illustrated in FIG. 3A, the port 320 may be a surgical tube. The patient introducer 301 may be secured to the platform 102 via a patient introducer holder 325. The patient introducer holder 325 may secure the position of the patient introducer 301 with respect to the platform 102 and may also reduce the force applied to the patient 101 by the patient introducer 301 by supporting at least a portion of the weight of the patient introducer 301. Although the patient introducer holder 325 is illustrated as being on the same side of the platform 102 as the patient introducer 301, in some embodiments, the patient introducer holder 325 may be located on the opposing side of the platform 102, or any other suitable location, such as the head of the platform 102 or from another platform suspended above the patient. During certain procedures, placement of the patient introducer holder 325 on the opposite side of the platform 102 with respect to the patient introducer 301 may be desirable since this placement may introduce fewer restrictions on the motion of the robotic arms 175. For example, the robotic arms 175 may be restricted from moving to the space occupied by the patient introducer holder 325 when the patient introducer holder 325 is located as illustrated in FIG. 3A. However, the described and illustrated placements of the patient introducer holder 325 are merely exemplary and the patient introducer holder 325 may be placed at any location(s) in which the patient introducer 301 is at least partially supported by the patient introducer holder 325.

The patient introducer 301 may include a proximal end 303 and a distal end 305, as well as an introducer tube 307 therebetween. The proximal end 303 of the patient introducer 301 forms a first opening (also referred to as an orifice) which may be configured to receive a surgical tool 115 (e.g., an endoscopic tool) and the distal end 305 of the patient introducer 305 forms a second opening which may be configured to guide the surgical tool 115 into the port 320. The introducer tube 307 connects the proximal and distal ends 303, 305 of the patient introducer 301 and guides the surgical tool 115 from the proximal end 303 to the distal end 305 of the patient introducer 301.

Between the first opening formed at the proximal end 303 of the patient introducer 301 and the second opening formed at the distal end 305 of the patient introducer 301, the introducer tube 307 may have a defined curvature to guide the distal end of the surgical tool 115 along the introducer tube 307 as the surgical tool 115 is advanced from the proximal end 303 to the distal end 305 of the introducer tube 307. This may enable the surgical robotic system 110 to manipulate the surgical tool 115 from a position that is not in direct axial alignment with the port 320, thereby allowing for greater flexibility in the placement of the cart 180 of the surgical robotic system 110 within the room. That is, without the curvature of the introducer tube 307, the robotic arms may be required to be substantially aligned with a major axis of the surgical tool above the patient's head. Further, the curvature of the introducer tube 307 may allow the robotic arms 175 of the surgical robotic system 110 to be substantially horizontally aligned with the patient introducer 301, which may facilitate manual movement of the robotic arm 175 if needed.

Figure 3B:
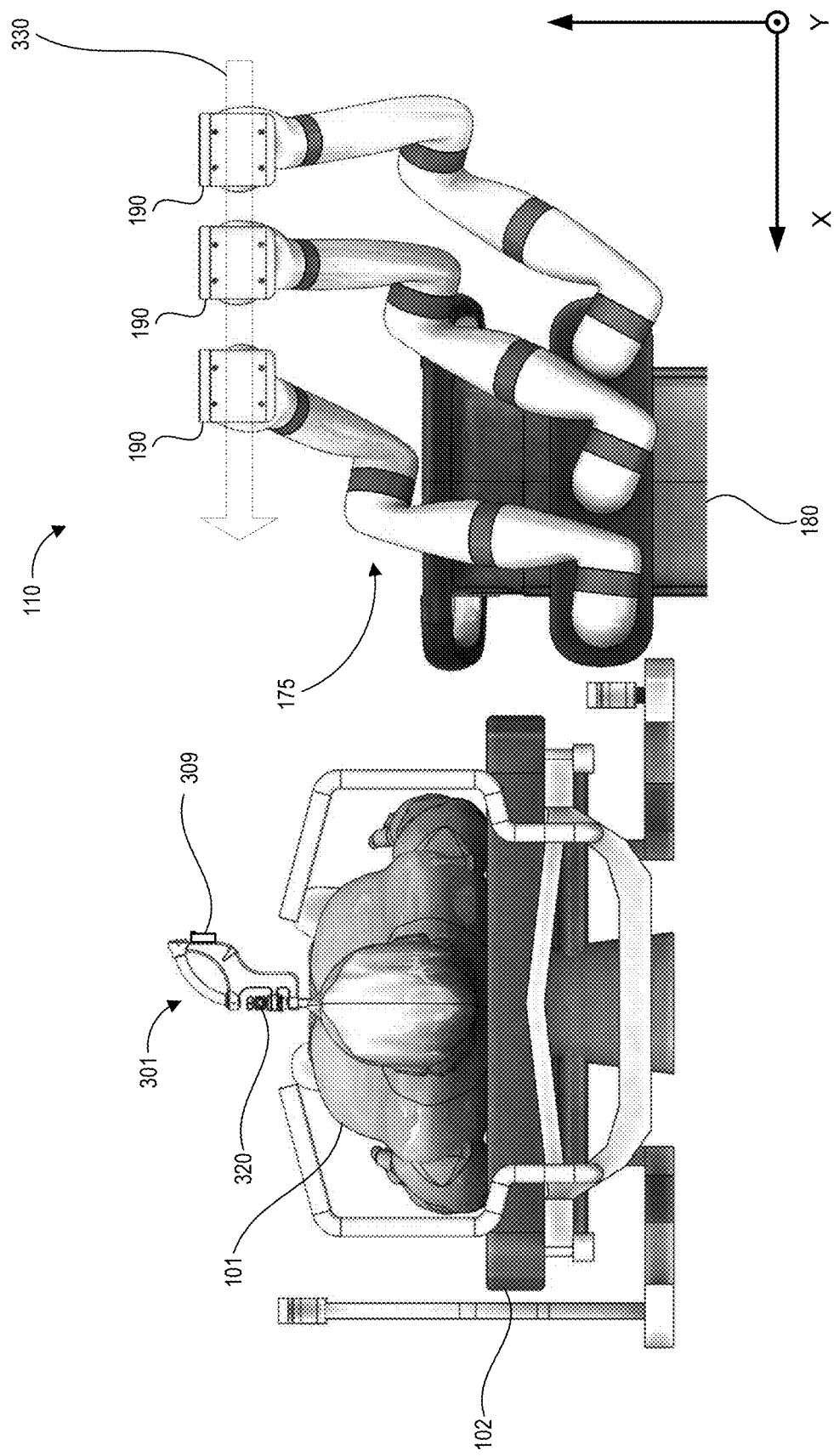
FIG. 3B illustrates an embodiment of a system and approach to aligning a surgical robotic system cart with a patient introducer in accordance with aspects of this disclosure.

FIG. 3B illustrates an example embodiment of a system and approach to aligning a surgical robotic system cart 180 with a patient introducer 301 in accordance with aspects of this disclosure. In this embodiment, the patient introducer 301 further includes an alignment member 309 which may aid in alignment of the robotic system cart 180 with the patient introducer 301. The robotic arms 175 of the surgical robotic system 110 may be configured to align to form a virtual rail 330, conceptually illustrated in FIG. 3B by a dashed arrow. The virtual rail 300 may have a major axis which may be aligned with the first opening in the proximal end 303 of the patient introducer 301 (see FIG. 3A). Additionally, the virtual rail may define a volume in space in which the manipulator assemblies (e.g., the IDMs 190) are configured to be arranged during manipulation of the surgical tool 115 (e.g., during a surgical procedure). Accordingly, alignment of the virtual rail 330 defined by the IDMs 190 with the patient introducer 301 may improve operational control of the surgical tool 115 during a surgical procedure as defined above.

As will be discussed in connection with the various embodiments thereof, the alignment member 309 provides a number of advantages to the patient introducer 301 over a patient introducer that does not include an alignment member 309. For example, the physical alignment of an IDM 190 with the alignment member 309 may facilitate increased accuracy and expedited alignment as compared to other alignment techniques. Proper alignment of the patient introducer 301 with the IDM 190 via the use of the alignment member 309 may prevent issues that may arise during the surgical procedure, such as, for example, elevated levels of friction or situations requiring manual assistance during the surgical procedure. Another possible result of misalignment that can be prevented is that the stroke length of the robotic arms 175 may be limited, which can limit the ability of the surgical robotic system 110 in controlling the distal end of the surgical tool 115 throughout the desired range of motion. Without the full range of motion, the surgical tool 115 may be prevented from accessing a target location within a luminal network 140, which may require realignment of the surgical robotic system cart 180 with the patient introducer 301 prior to performing the surgical procedure again.

Furthermore, as mentioned above, the alignment member 309 of the patient introducer 301 may be configured to aid in the alignment of components of the surgical robotic system 110 with the patient introducer 301. In at least one embodiment, the alignment member 309 may be configured to physically contact one of the IDMs 190 and/or may include markings (also referred to as markers) for which complementary markings may be formed on at least one IDM 190 to facilitate the alignment.

Alignment of the IDM 190 with the patient introducer 301, via the use of the alignment member 309, may be geometrically defined by the six degrees of freedom of movement for a body within three-dimensional space. That is, if the patient introducer 301 is considered to be a fixed point in space, the alignment of the IDM 190 with the patient introducer 301 can be specified by providing values for the six degrees of freedom of movement of the IDM 190 with respect to the patient introducer 301. These degrees of freedom may include the positions (e.g., forward/backward (the X-axis), left/right (the Y-axis), up/down (the Z-axis) as illustrated in FIG. 3B) and/or the orientation (e.g., pitch (rotation around the Y-axis), yaw (rotation around the Z-axis), and roll (rotation around the X-axis)) of the IDM 190. Although the positional axes (X-axis, Y-axis, and Z-axis) may be defined, located, and/or oriented in various different manners, this disclosure will refer to these axes as illustrated in FIG. 3B throughout the disclosure. Aspects of the present disclosure relate to methods and techniques for placing the IDM 190 into an alignment position/orientation with respect to the patient introducer 301 to align the IDM 190 with the patient introducer 301. The surgical robotic system 110 may record the spatial position and/or orientation of the IDM 190 during alignment so that the surgical robotic system 110 is aware of the spatial position and/or orientation of the patient introducer 301 during a surgical procedure.

Alignment of the IDM 190 with the patient introducer 301 may also be defined by the alignment of one or more axes of the IDM 190 with one or more axes of the patient introducer 301. For example, the patient introducer 301 may define an axis (which may be referred to as a receive axis herein) along which the patient introducer 301 is configured to receive the surgical tool 115. Similarly, the IDM 190 may have an axis defined by the virtual rail 330 (discussed above). In certain embodiments, alignment of the IDM 190 with the patient introducer 301 may be defined when the receive axis of the patient introducer 301 is substantially aligned with the virtual rail 330 of the IDM 190.

Example Implementations of the Alignment Member

Figure 4A:
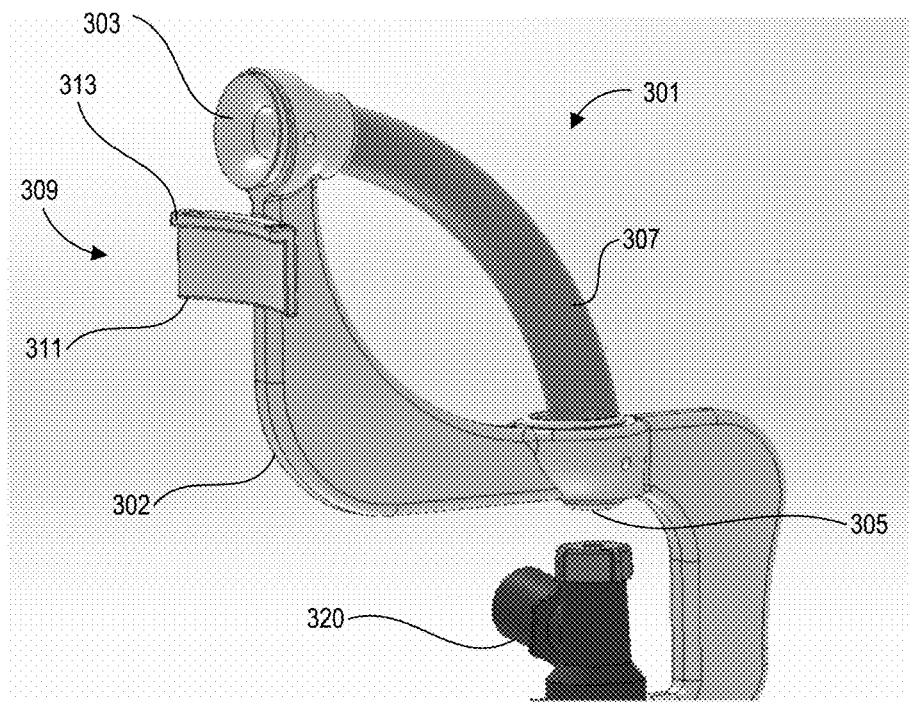
FIGS. 4A and 4B illustrate an embodiment of an alignment member for use during an alignment procedure in accordance with aspects of this disclosure.
Figure 4B:
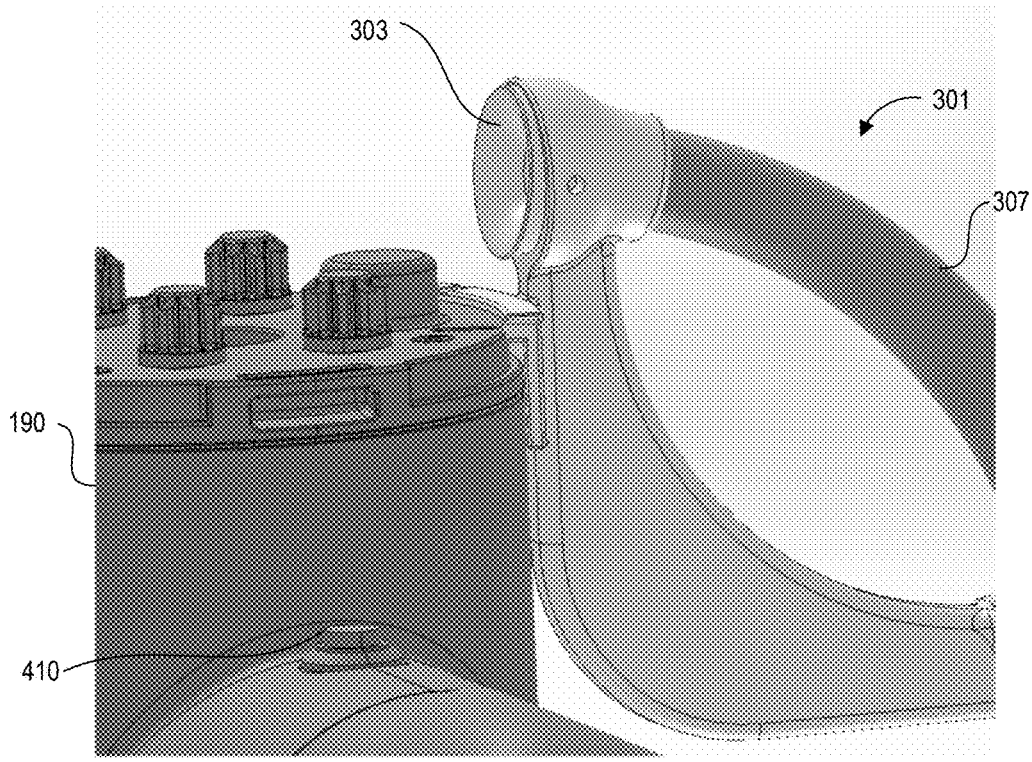

FIGS. 4A-B and 5A-H illustrate different embodiments of the alignment member 309 and IDM 190 in accordance with aspects of this disclosure. FIGS. 4A and 4B respectively illustrate an embodiment of the alignment member 309 on its own and the alignment member 309 in contact with an IDM 190 during an alignment procedure.

With reference to FIGS. 4A and 4B, the patient introducer 301 includes an alignment member 309 attached to the body 302 or supporting structure of the patient introducer 301. The alignment member 309 may be positioned proximal to the proximal end 303 of the introducer tube 307. This location for the alignment member 309 may facilitate alignment of the opening defined in the proximal end 303 with an IDM 190 via physical contact between the alignment member 309 and the IDM 190. However, in other embodiments, the alignment member 309 may be attached to the patient introducer 301 at other locations or may be attached to the patient introducer holder 325. For example, when the distance between the alignment member 309 and the opening defined in the proximal end 303 of the introducer tube 307 is known, the surgical robotic system 110 may be able to accurately calculate the positioning of the IDM 190 with respect to the opening defined by the proximal end 303 of the patient introducer 301 in response to an alignment of the IDM 190 with the alignment member 309.

The alignment member 309 may include physical features, markings and/or other alignment components to aid in alignment with the IDM 190. In one implementation, the alignment member 309 may include a first curved surface 311 and an elongated protrusion 313. The shape defined by the first curved surface 311 and the elongated protrusion 313 may form a complementary shape to an external surface of the IDM 190. As such, the IDM 190 may be at least partially aligned with the alignment member 309 by bringing the IDM 190 into close physical contact with (e.g., interfacing with) the alignment member 309, as shown in FIG. 4B. For example, after an external curved surface of the IDM 190 contacts the first curved surface 311 and an upper surface of the IDM 190 contacts the elongated protrusion 313, the positioning of the IDM 190 in space with respect to the alignment member 309 may be defined by restricting further movement of the IDM 190 past the first curved surface 311 and the elongated protrusion 313. Additionally, as shown in FIG. 4B, the upper surface of the IDM 190 which contacts the elongated protrusion 313 may not be the highest surface defined by the IDM 190, but may be defined by a recess. In other embodiments, the upper surface of the IDM 190 which contacts the elongated protrusion 313 may be defined by a protrusion in the upper surface of the IDM 190 or may be flush with the remainder of the upper surface. Similarly, the external curved surface of the IDM 190 which contacts the first curved surface 311 may be flush with the external surface of the IDM, formed as a recess, or formed as a protrusion. Additional exemplary embodiments will be discussed in detail below.

While the first curved surface 311 of the alignment member 309 remains in contact with the external curved surface of the IDM 190 (e.g., a majority of the first curved surface 311 is in contact or in close contact with the external curved surface), the alignment of the alignment member 309 with the IDM 190 is restricted in four degrees of freedom (e.g., in the X and Y-axes as well as in the pitch and roll orientations). The elongated protrusion 313 may be used to restrict orientation of the alignment member 309 with the IDM 190 in the Z-axis degree of freedom.

The physical contact between the IDM 190 and the alignment member 309 may be sufficient to define the spatial positioning of the IDM 190 with respect to the alignment member 309; however, in some embodiments, the physical contact may not be sufficient for complete rotational alignment therebetween in each of the rotational degrees of freedom (e.g., in the yaw orientation). For example, in the FIG. 4B embodiment, the IDM 190 may be free to rotate around the Z-axis while maintaining contact with the alignment member 309. Accordingly, in some embodiments, the alignment member 309 and/or the IDM 190 may further comprise alignment markings to define the rotational alignment of the IDM 190 with the alignment member 309.

Figure 5D:
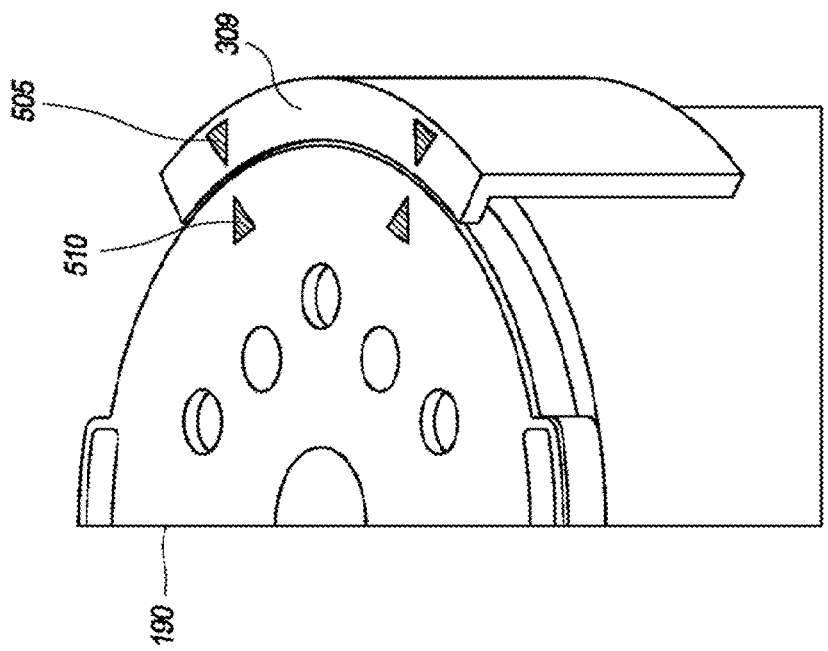

FIGS. 5A-5H illustrate a number of embodiments of alignment markings which may be used to aid in rotational alignment of a manipulator assembly (e.g., the IDM 190) with the alignment member 309. In the embodiment of FIGS. 5A and 5B, the alignment member 309 includes a first set of alignment markings 505 and the IDM 190 includes a second set of alignment markings 510 corresponding to the first set of alignment markings 505. After the alignment member 309 has been brought into contact with the IDM 190 (as in FIG. 5B), the IDM 190 and the alignment member 309 can be rotationally aligned, with respect to rotation about the Z-axis (e.g., the yaw of the IDM 190), by aligning the first and second sets of alignment markings 505 and 510. In the embodiment of FIGS. 5A and 5B, the first and second sets of alignment markings 505 and 510 may be formed as bands. The alignment bands may be embodied by various different shapes, sizes, dimensions, tolerances, etc. in order to aid in the yaw orientation alignment of the IDM 190 with the alignment member 309. Certain embodiments of the bands are illustrated in FIGS. 5A, 5B, and 5E-H; however, the design of the bands is not limited thereto and the bands may have any shape, size, dimension, tolerance, etc. for alignment in the yaw orientation.

Figure 5C:
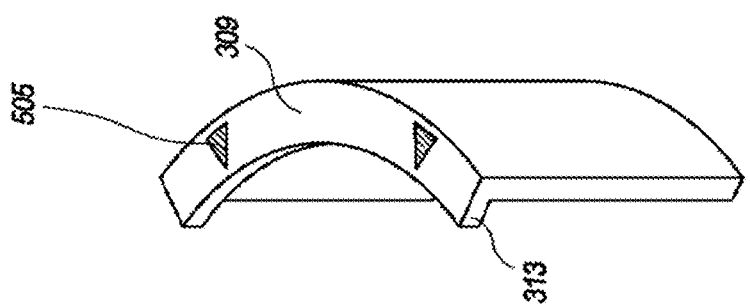
Figure 5C:
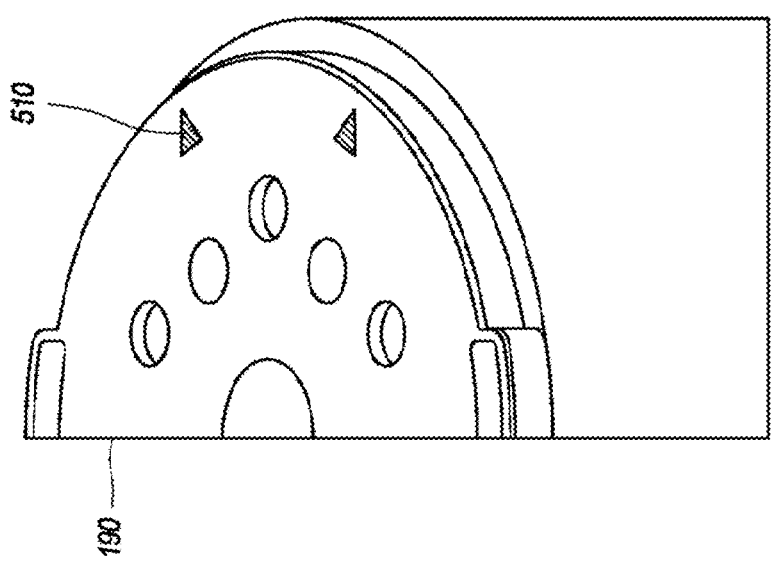

In the embodiment of FIGS. 5C and 5D, the first and second sets of alignment markings 505 and 510 may be formed as opposing triangles. In this embodiment, the points of the triangles may be matched up to confirm that rotational alignment between the IDM 190 and the alignment member 309 is complete. As shown in FIGS. 5C and 5D, the alignment markings 505 may be formed on the elongated protrusion 313.

Figure 5H:
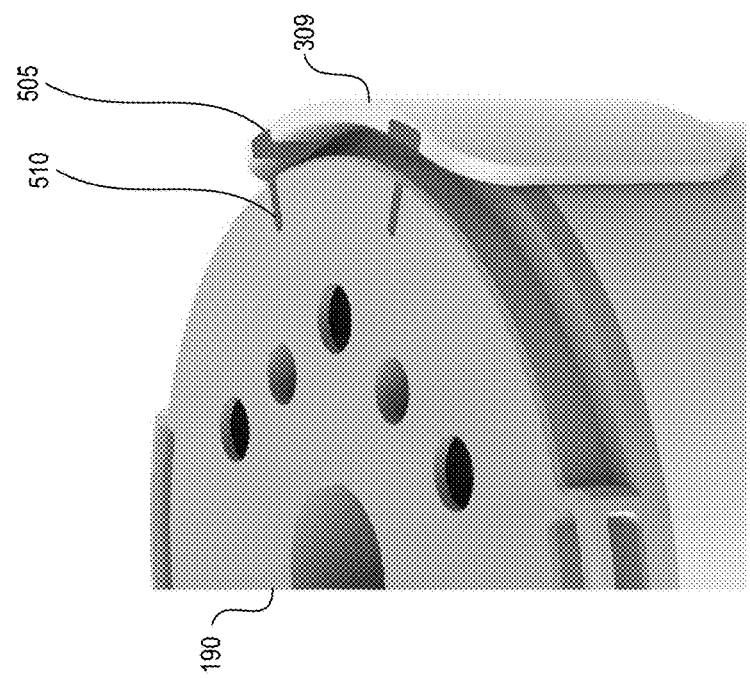
Figure 5G:
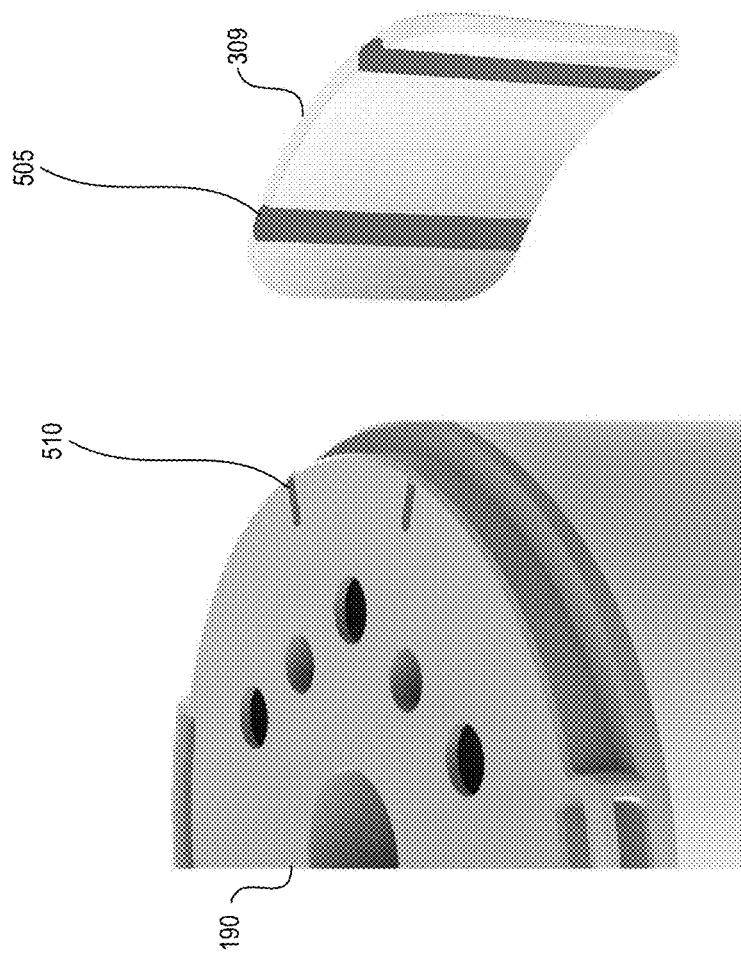

Another embodiment, as illustrated in FIGS. 5E and 5F, includes a single first alignment marking 505 and a single second alignment marking 510. In this embodiment, the first and second alignment markings 505 and 510 form wider bands than in the embodiment of FIGS. 5A and 5B. Here, rotational alignment between the IDM 190 and the alignment member 309 may be achieved when the ends of the bands are substantially aligned with each other. In yet another embodiment, as shown in FIGS. 5G and 5H, the first alignment markings 505 may be wider than the second alignment markings 510. In this embodiment, the IDM 190 may be rotationally aligned with the alignment member 309 when the second alignment markings 510 are within the widths defined by the bands of the first alignment markings. Here, the difference in widths between the first and second alignment markings 505 and 510 may correspond to a tolerance range for rotational alignment with respect to rotation around the Z-axis. The tolerance range defined by the widths of the alignment markings 505 and 510 may ensure that the surgical robotic system is able to fully manipulate the surgical tool at any position defined within the tolerance range. Additionally, in other embodiments, the second alignment markings 510 formed on the IDM 190 may be wider than the first alignment markings 505. Although the tolerance range has been discussed in connection with the embodiment where the tolerance range is defined by the widths of the alignment markings 505 on the alignment member 309, the indication of the tolerance range may vary and differ across difference embodiments and markings. For example, the tolerance range may be defined by the first alignment markings 505 on the alignment member 309, by the second alignment markings 510 on the IDM 190, and/or by a combination thereof etc. Furthermore, the indication of the tolerance range may be located on the patient introducer 301, the IDM 190, a sterile adaptor, etc.

The first alignment markings 505 and the second alignment markings 510 may also be positioned on the alignment member 309 and the IDM 190 at locations which enable a user of the robotic surgical system to visually confirm rotational alignment from a number of different vantage points. For example, as shown in FIG. 4B, the IDM 190 may have a number of components which protrude from the upper surface of the IDM 190. These protrusions, and/or other objects such as the patient introducer itself, may block the view of one or more of the first and second alignment markings 505 and 510 depending on where the user is standing. Accordingly, the first and second alignment markings 505 and 510 may be placed at different locations on the alignment member 309 and the IDM 190 such that at least one of each of the first and second alignment markings 505 and 510 is viewable by the user when viewed from one of a plurality of vantage points. This may enable the user to visually confirm the rotational alignment of the IDM 190 and the alignment member 309 without requiring the user to move in order to see the first and second alignment markings 505 and 510.

Additionally, when the manipulator assembly includes an additional component attached to the IDM 190, such as a sterile adaptor, a third set of alignment markings (not illustrated) may be formed on the additional component so that the additional component can be aligned with the alignment member. The third markings may be formed on the additional component in a manner similar to the second markings 510 illustrated in FIGS. 5A-5H. In these embodiments, the sterile adaptor may include at least a portion with a surface that complements the shape of the alignment member 309. The sterile adaptor may be an adaptor configured to be physically attached to the IDM 190 for surgical procedures which require the interface between the IDM 190 and the robotic arm 175 to be sterile. In certain embodiments, the sterile adaptor may have an exterior surface and/or surgical tool interface that is substantially the same as or similar to that of the interface between the IDM 190 and the surgical tool 115.

Additional Alignment Techniques

In certain aspects of this disclosure, additional alignment techniques may be employed in place of or in addition to the physical alignment embodiments discussed in connection with FIGS. 4 and 5. These techniques may assist in the manual or automatic alignment of the IDM 190 with the patient introducer 301.

In one example, a radio-frequency identification (RFID) reader and RFID tag may be used to aid in alignment. The patient introducer 301 may include an RFID tag positioned on the alignment member 309 or another location on the patient introducer 301. The IDM 190 may include an RFID reader configured to read a wireless signal transmitted from the RFID tag. In other embodiments, the positions of the RFID tag and RFID reader may be exchanged.

The RFID tag may be a passive device which collects energy emitted from the RFID reader and may transmit an RFID signal using the power collected from the RFID reader. By detecting the signal transmitted from the RFID tag, the RFID reader may be able to determine the position of the RFID reader with respect to the RFID tag. Additionally, as the RFID reader moves closer to the RFID tag, the signal detected by the RFID reader may become stronger. Accordingly, when the RFID reader finds a maximum (or peak) in the strength of the signal received from the RFID tag, the RFID reader may be able to infer that the RFID tag is at a closest possible position to the RFID reader. The strength of the received RFID signal may be displayed to a user, for example, via display modules 202, in order to aid in the manual alignment of the IDM 190 with the patient introducer 301. Alternatively, the RFID signal may be used as an input by a processor of the surgical robotic system for the automatic alignment of the IDM 190 with the patient introducer 301.

In another example, the surgical robotic system 110 may include a laser tracking system to aid in alignment. For example, the IDM 190 may include a laser emitter (also referred to simply as a laser) and a laser light sensor, while a laser reflector is positioned on the patient introducer 301 (e.g., on the alignment member 309). The laser, laser reflector, and laser light sensor may be positioned such that laser light is reflected onto the sensor when the IDM 190 is properly aligned with the patient introducer 301. As such, the positioning of the laser and laser light sensor with respect to the laser reflector enable the surgical robotic system 110 to determine that the IDM 190 has been aligned with the patient introducer 301.

In an alternative embodiment, the IDM 190 includes at least one laser and the patient introducer 301, or the alignment member 309, includes at least one alignment marking corresponding to the laser. The user of the surgical robotic system 110 may then determine that the IDM 190 is aligned with the patient introducer 301 by visually confirming that the laser light falls on the at least one alignment marking. In these embodiments, the placement of the laser, laser reflector, laser light sensor, and the at least one marking may be exchanged between the IDM 190 and the patient introducer 301. In certain embodiments, there may be at least three lasers and three markings/sensors in order to ensure that the alignment between the IDM 190 and patient introducer 301 is defined in all degrees of freedom. In certain embodiments, there may be at least one laser and at least one marking/sensor in order to ensure that the alignment between the IDM 190 and patient introducer 301 is defined in all degrees of freedom.

In another example, the alignment member 301 may include a light-emitting diode (LED) configured to emit light based on a positioning of the LED relative to a photodiode placed on the IDM 190. For example, the photodiode place on the IDM 190 may be able to sense light emitted from the LED in order to determine the alignment of the IDM 190 with respect to the alignment member 301. Additionally, in certain embodiments, the alignment member 301 may include a plurality of LEDs respectively corresponding to a plurality of photodiodes positioned on the IDM 190. When the photodiodes detect light received from the respective LEDs, the IDM 190 may be able to determine that the IDM 190 has been aligned with the alignment member. Further, the LEDs may have different colors while the photodiodes may have corresponding color filters. Thus, only light from a corresponding one of the LEDs may be detected by the photodiodes.

In another example, the alignment of the IDM 190 with the patient introducer 301 may include the use of acoustic reflection. For example, the IDM 190 may include an acoustic emitter and an acoustic sensor, while the patient introducer 301 and/or alignment member 309 includes an acoustic reflector. The IDM 190 may then be positioned based on the signal detected by the acoustic sensor, where a maximum value of the measured signal is indicative of the IDM 190 being aligned with the patient introducer 301.

In another example, a magnetic field sensor may be placed on the IDM 190 with a magnet placed on the patient introducer 301 and/or alignment member 309. The signal measured by the magnetic sensor may be used to determine the positional alignment of the IDM 190 with the patient introducer. The placement of these elements may be exchanged between the IDM 190 and patient introducer 301.

In one implementation, the alignment of the IDM 190 with the patient introducer 310 may further involve the use of an EM generator and an EM sensor or EM sensors. For example, the manipulator assembly may include an EM sensor and an EM generator may be arranged on or adjacent to the platform 102. The surgical robotic system 110 may use the signal detected by the EM sensor to determine the position of the IDM 190 with respect to the EM generator.

In yet further embodiments, the physical shape of the alignment member 309 and the IDM 190 may be altered from the embodiments discussed in connection with FIGS. 4 and 5. For example, the alignment of three points on the patient introducer 301 with three corresponding points on the IDM 190 may be sufficient to define alignment therebetween. Thus, in one example, the patient introducer 301 may include three elongated protrusions while the IDM 190 may include three markings corresponding thereto. When the elongated protrusions are in contact with the corresponding markings on the IDM 190, the patient introducer 301 may be aligned with the IDM 190. Alternatively, the elongated protrusions may be formed on the IDM 190, with the markings on the patient introducer 301, or each of the IDM 190 and patient introducer may include three protrusions configured to meet in space with the corresponding protrusions on the opposing element.

Although a number of examples of different sensors which may be used to aid a user in aligning the IDM 190 with the patient introducer 301 and/or for automatic alignment of the IDM 190 with the patient introducer 301 performed by the surgical robotic system 110, other types of sensor may also be used in addition to or in place of the sensors described herein. For example, alignment may be performed using any other sensor modality, including but not limited to vision shape matching using optical sensor(s) (e.g., camera(s)), ultrasound sensor(s), accelerometer(s), capacitive coupling sensor(s), etc.

Another method for physical alignment between the patient introducer 301 and the IDM 190 may be the use of a protrusion and hollow cavity. Thus, when the protrusion is inserted into the hollow cavity, the patient introducer 301 and IDM 190 may be aligned. Since a simple cylindrical protrusion and hollow cavity may not define rotational alignment along the major axis of the protrusion, the protrusion/hollow cavity may be keyed such that only one rotational alignment therebetween will allow the protrusion to be inserted into the cavity.

Example Methods for Alignment

Figure 6:
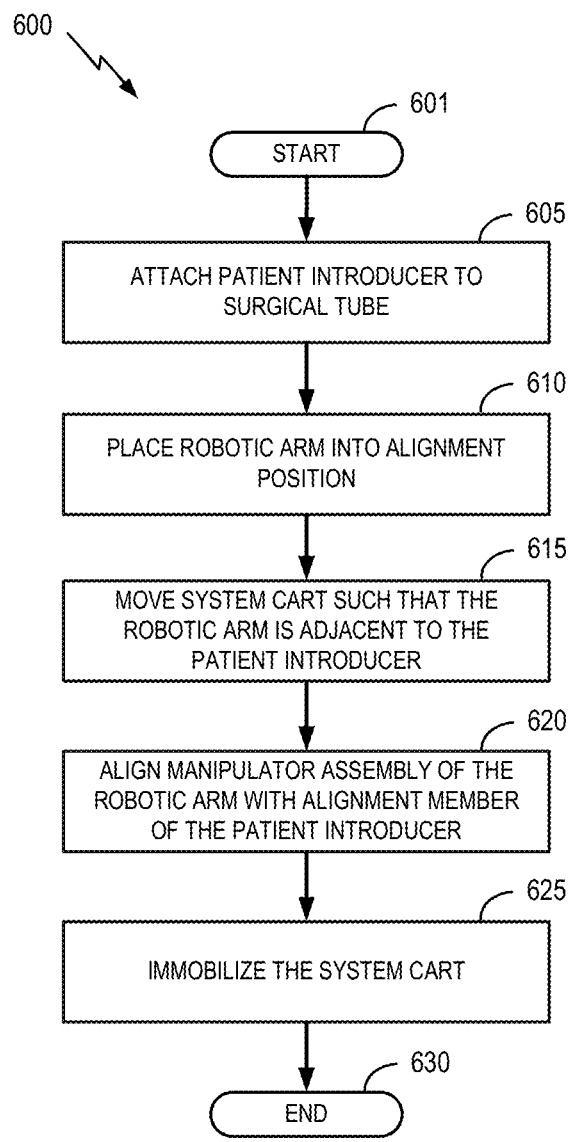
FIG. 6 provides a flowchart illustrating an example methodology of aligning of a surgical robotic system cart with a patient introducer in accordance with aspects of this disclosure.

Example methods for aligning a surgical robotic system cart with a patient introducer will now be described in connection with FIGS. 6-10. FIG. 6 provides an overview of the alignment of the system cart with the patient introducer. Aspects of each of the methods disclosed hereinafter, e.g., methods 600-1000, can be implemented by a human operator manually manipulating the IDM 190 or other components of a surgical robotic system, the surgical robotic system itself (such as system 110 described above) mechanically manipulating the IDM 190 as directed by a human operator or autonomously, or a combination thereof.

Method 600 begins at block 601. At block 605, the patient introducer 301 is attached to a port 320. The port 320 may be been previously placed in a patient 101 by medical staff. At block 610, the robotic arm 175 is placed into an alignment pose. This may be performed automatically by the surgical robotic system 110 in response to an input command from the user, or the user may manually guide the robotic arm 175 into the alignment pose. When guided by the user, the surgical robotic system may provide feedback to the user indicative of when the robotic arm 175 is in or within a threshold distance of the alignment position.

At block 615, the user may optionally move the system cart 180 (in embodiments that utilize a system cart) such that the robotic arm 175 is adjacent to the patient introducer 301. This step may be considered a coarse alignment of the system cart 180 with the patient introducer. Since the robotic arms 175 have a limited range of motion, if the system cart 180 is not placed sufficiently close to the patient introducer prior to alignment, the robotic arm 175 may not be able to reach the patient introducer for alignment. Block 620 involves aligning (spatially and/or rotationally) the manipulator assembly (e.g., the IDM 190) of the robotic arm 175 with an alignment member 309 of the patient introducer 301. This step may be done manually by the user, automatically by the surgical robotic system 110, or by a combination of manual and automatic procedures. The surgical robotic system 110 may store the position of the IDM 190 (e.g., an alignment position) in response to the IDM 190 being aligned with the patient introducer 301. The storing of the alignment position of the IDM 190 may be performing in response to the surgical robotic system 110 receiving a confirmation from the user that the IDM 190 is aligned with the patient introducer 301.

In certain embodiments, the patient introducer 301 may be moved into alignment with the IDM 190. For example, the platform 102 supporting the patient 101 may be moveable (e.g., having lockable/unlockable wheels) and/or adjustable within the operating environment 100 to facilitate alignment with the IDM 190. Accordingly, the platform 102 may be moved into position such that the patient introducer 301 is aligned with the IDM 190. In some embodiments, alignment of the IDM 190 with the patient introducer 301 may involve moving both the IDM 190 and the patient introducer 301. Once the manipulator assembly 190 has been aligned with the patient introducer 301, at block 625, the user may optionally immobilize the surgical robotic system cart 180. Alternatively, if the surgical robotic system cart 180 includes automated brakes and/or an actuator for moving the cart 180, the surgical robotic system 110 may automatically immobilize the system cart 180. In some embodiments, such as where the robotic arm 175 is not positioned on a system cart 180 (e.g., when the robotic arm 175 is positioned on the table), blocks 615 and 625 may not be performed. The method 600 ends at block 630.

Figure 7:
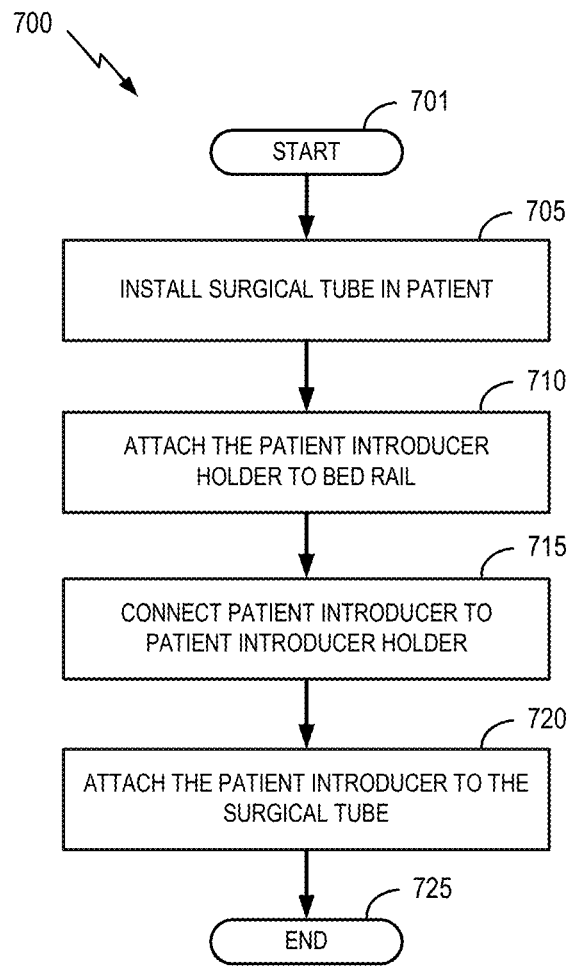
FIGS. 7-10 provide flowcharts illustrating examples of further aspects of the alignment methodology of FIG. 6.

FIG. 7 provides a flowchart illustrating a method 700 providing additional aspects related to block 605 of FIG. 6. The method 700 begins at block 701. At block 705, a port 320 is installed into the patient. Block 705 may be performed by medical staff in preparing for a surgical procedure to be performed by/using the surgical robotic system 110. At block 710, the medical staff may attach and/or secure the patient introducer holder 325 to a bed rail or other secure portion of the platform 102. Examples of the secure portion of platform 102 to which the patient introducer holder 325 may be attached include: a bed frame, a support column, a pad placed underneath the patient 101, etc. This may secure the patient introducer 301, reducing the chance of the patient introducer 301 shifting or otherwise moving out of position during alignment or the surgical procedure. At block 715, the medical staff connects the patient introducer 301 to a patient introducer holder 325. In other embodiments, the patient introducer 301 may be aligned with the port 325 without being directly connected thereto, for example, the patient introducer 301 may be secured adjacent to and in alignment with the port 325.

At block 720, the medical staff attaches the patient introducer 301 to the port 320. This step may be performed simultaneously with block 715, for example, the final position of the secured patient introducer holder 325 may not be set until after the patient introducer 301 has been connected to the port 320. The method 700 ends at block 725.

Figure 8:
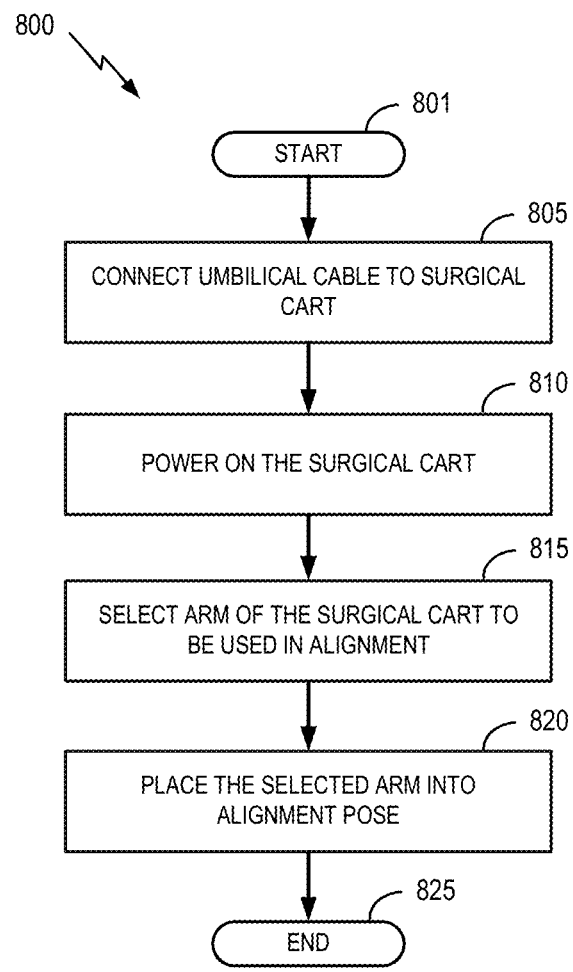

FIG. 8 is a flowchart illustrating a method 800 providing additional aspects related to block 610 of FIG. 6. The method 800 begins at block 801. At block 805, the user connects an umbilical cable to the surgical robotic system cart 180. The umbilical cable may provide communication and/or power to the surgical robotic system cart 180. At block 810, the user powers on the robotic surgical system cart 180. At block 815, the user may select one of a plurality of robotic arms 175 of the robotic surgical system cart 180 to be used in alignment with the patient introducer 301. The selected robotic arm 175 may be the closest arm 175 to the patient 101 and/or bed 102. At block 820, the user places the selected robotic arm 175 into the alignment pose. In other embodiments, the user may input a command to the surgical robotic system 110 to have the surgical robotic system 110 automatically position the robotic arm 175 into the alignment pose. The method 800 ends at block 825.

Figure 9:
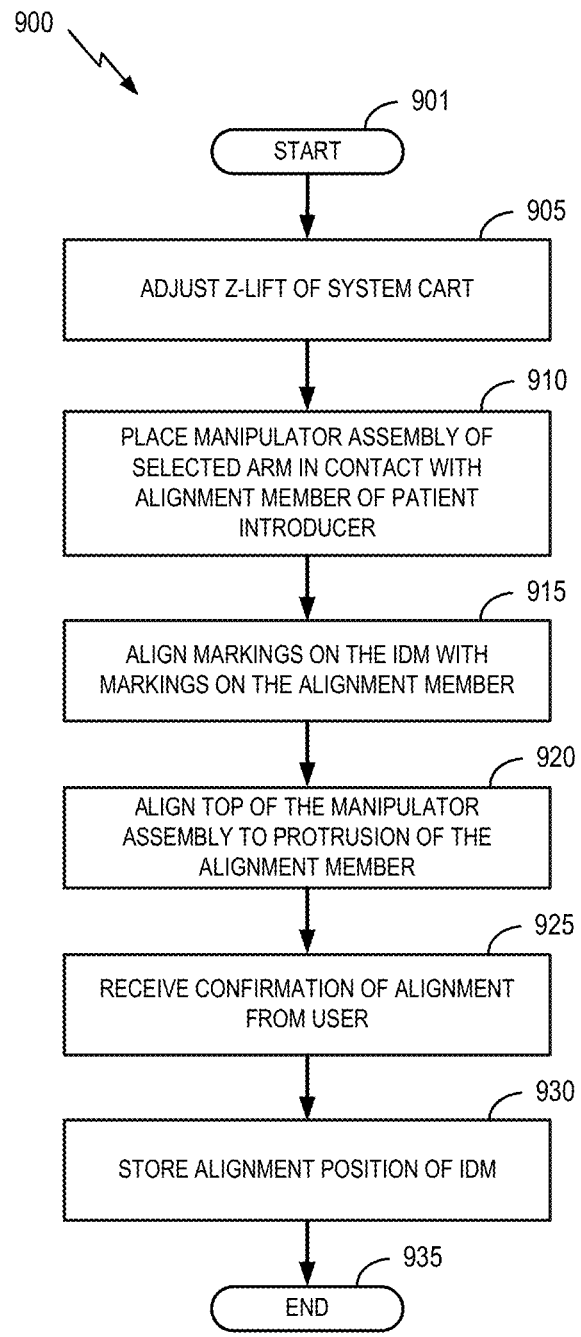

FIG. 9 provides a flowchart for a method 900 providing additional aspects related to block 620 of FIG. 6. The method 900 begins at block 901. At block 905, the user and/or the surgical robotic system 110 adjusts the Z-lift of the surgical robotic system cart 180. This may involve adjusting the height of the system cart 180 to a level suitable for the height of the platform 102. At block 910, in a manual embodiment, the user places the manipulator assembly (e.g., IDM 190) of the selected robotic arm 175 in contact with the alignment member 309 of the patient introducer 301. The user may be required to press an admittance button to allow for the manual manipulation of the robotic arm 175.

Depending on the embodiment, block 910 may be performed automatically by the surgical robotic system 110 using one or more sensors as inputs for feedback during the alignment. In some embodiments, the alignment of the manipulator assembly with the patient introducer 301 may not involve physical contact therebetween. For example, in embodiments where the IDM 190 includes a laser and laser light sensor, the surgical robotic system 110 may use the detection of laser light emitted from the laser, reflected off of the alignment member 309, and detected at the laser light sensor in automatically determining whether the IDM 190 is aligned with the alignment member 309. In embodiments that include the use of LED(s), the robotic surgical system may determine that the IDM 190 is aligned with the alignment member 309 when photodiode placed on the IDM 190 detects light received from the LED. Additionally, any of the alignment features and/or sensors discussed above may also be used in the automatic alignment of the IDM 190 with the patient introducer 301 by the surgical robotic system 110.

At block 915, the user/surgical robotic system aligns the markings on the manipulator assembly with the markings on the alignment member. In the embodiments of FIGS. 5A-5H, this may involve rotating the manipulator assembly 190 with respect to the Z-axis until the markings are aligned. In some embodiments, alignment of the markings on the manipulator assembly with the markings on the alignment member 309 may involve moving the manipulator assembly with respect to the alignment member 309 until the alignment markings of the manipulator assembly are alignment with the alignment markings of the alignment member 309. At block 920, the user/surgical robotic system aligns the top of the manipulator assembly to the elongated protrusion 313 of the alignment member 309. In certain embodiments, block 920 may be performed prior to or currently with block 915.

At block 925, the surgical robotic system 110 receives confirmation from the user that the alignment process has been completed. In other embodiments, the surgical robotic system 110 may automatically confirm that the alignment has been completed, and thus, does not require user input from the user, or the surgical robotic system 110 may perform the alignment automatically, not requiring any user input to confirm or perform alignment. At block 930, the surgical robotic system 110 stores the alignment position and orientation of the IDM 190 (e.g., the six degrees of freedom defining the final position of the IDM 190 after the alignment procedure) in memory. The stored alignment position may be used by the surgical robotic system 110 to calibrate the control and/or movement of the IDM 190 during the following surgical procedure. The method 900 ends at block 925.

Figure 10:
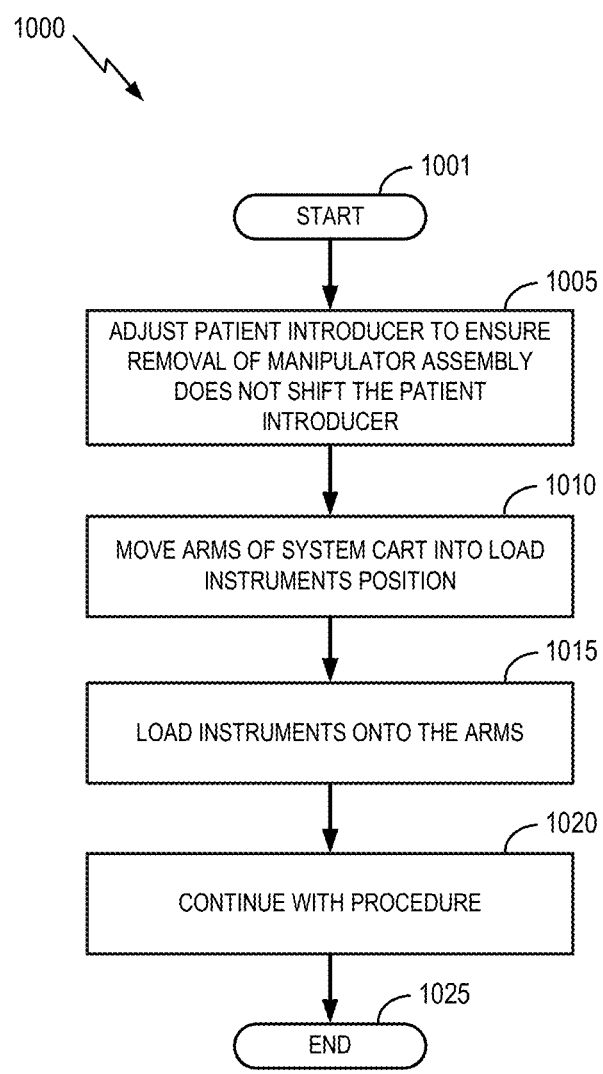

FIG. 10 provides a flowchart for a method 1000 providing additional aspects related to block 625. The method 1000 begins at block 1001. At block 1005, the user adjusts the patient introducer 301 to further secure the position of the patient introducer 301, preventing the patient introducer from shifting after the alignment procedure. For example, the patient introducer 301 may be secured by tightening a clamp (not illustrated) on the patient introducer holder 325. At block 1010, the user moves the robotic arms 175 into a load instruments position. Block 1010 may also be performed automatically by the surgical robotic system 110. At block 1015, the user loads the instruments to be used during the surgical procedure onto the robotic arms 175. At block 1020, the user continues with the surgical procedure. The method 1000 ends at block 1025.

Implementing Systems and Terminology

Implementations disclosed herein provide systems, methods and apparatus for alignment of a surgical robotic system cart with a patient introducer.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The robotic motion actuation functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A patient introducer, comprising:
   an introducer tube extending between (i) a distal end configured to be connected to a port and (ii) a proximal end configured to receive a surgical tool, the introducer tube having a curvature that defines a curved path and configured to introduce the surgical tool into a patient via guiding the surgical tool into the port along the curved path;
   a body directly connected to each of the distal end and the proximal end of the introducer tube; and
   an alignment member directly connected to the body and comprising a first shape and a first alignment marking, the alignment member configured to interface with a manipulator assembly of a robotic system, the manipulator assembly comprising a second shape and a second alignment marking, the first shape being complementary to the second shape,
   wherein the first alignment marking of the alignment member, when aligned with the second alignment marking, facilitates rotational alignment of the alignment member and the manipulator assembly.

2. The patient introducer of claim 1, wherein the manipulator assembly comprises an instrument device manipulator (IDM) connected to a distal portion of a first arm of the robotic system.

3. The patient introducer of claim 2, wherein:
   the manipulator assembly further comprises a sterile adaptor, and
   the second alignment marking is positioned on the sterile adaptor.

4. The patient introducer of claim 2, wherein the alignment member comprises:
   a first curved surface complementary to a second curved surface of the IDM; and
   an elongated protrusion complementary to an upper surface of the IDM,
   wherein the first curved surface and the elongated protrusion are configured to restrict movement of the IDM in at least one dimension.

5. The patient introducer of claim 4, wherein:
   the first alignment marking comprises a plurality of first alignment markers located on the alignment member,
   the second alignment marking comprises a plurality of second alignment markers located on the IDM,
   each of the first alignment markers is configured to be aligned with a corresponding one of the second alignment markers, and
   the first alignment markers are arranged on the alignment member such that, in use, at least one of the first alignment markers is not obstructed from view by the IDM when viewed from one of a plurality of vantage points.

6. The patient introducer of claim 4, wherein:
   the first alignment marking comprises a first band located on an upper surface of the elongated protrusion of the alignment member,
   the second alignment marking comprises a second band formed on the upper surface of the IDM, and
   the first band has a width that is greater than a width of the second band, the width of the first band corresponding to a tolerance range for rotational alignment of the IDM with the alignment member.

7. The patient introducer of claim 2, wherein:
   the alignment member is further configured to interface with a sterile adaptor connected to the IDM, the sterile adaptor comprising a third alignment marking,
   alignment of the first alignment marking of the alignment member with the third alignment marking of the sterile adaptor, in use, facilitates rotational alignment of the alignment member and the sterile adaptor.

8. The patient introducer of claim 2, wherein alignment of the first alignment marking of the alignment member with the second alignment marking of the IDM, in use, defines an initial position of the IDM with respect to the alignment member in six degrees of freedom.

9. The patient introducer of claim 1, wherein:
   the alignment member comprises a radio-frequency identification (RFID) tag,
   the manipulator assembly comprises an RFID reader, and
   positioning of the alignment member and the manipulator assembly, in use, based on a RFID signal between the RFID reader and RFID tag, facilitates the rotational alignment of the alignment member with the manipulator assembly.

10. The patient introducer of claim 1, wherein:
    the introducer is configured to be connected to the port via the body.

11. A method of positioning a patient introducer and a robotic arm of a surgical robotic system, the method comprising:
    aligning a patient introducer to a port, the patient introducer comprising:
    an introducer tube extending between (i) a distal end configured to be connected to the port and (ii) a proximal end configured to receive a surgical tool, the introducer tube having a curvature that defines a curved path and configured to introduce the surgical tool into a patient via guiding the surgical tool into the port along the curve path,
    a body directly connected to each of the distal end and the proximal end of the introducer tube, and
    an alignment member directly connected to the body and comprising a first shape and a first alignment marking, the alignment member configured to interface with a manipulator assembly of the surgical robotic system;

placing the robotic arm into an alignment position, the manipulator assembly being connected to a distal portion of the robotic arm, the manipulator assembly comprising a second shape and a second alignment marking, the second shape being complementary to the first shape; and rotationally aligning the manipulator assembly and the alignment member based on aligning the second alignment marking of the manipulator assembly with the first alignment marking of the alignment member.

12. The method of claim 11, wherein the alignment member comprises:

a first surface complementary to a second surface of the manipulator assembly; and an elongated protrusion complementary to an upper surface of the manipulator assembly, wherein the first surface and the elongated protrusion are configured to restrict movement of the manipulator assembly in at least one dimension.

13. The method of claim 12, wherein aligning the manipulator assembly and the alignment member comprises:

moving the manipulator assembly such that the second surface of the manipulator assembly is in contact with the first surface of the alignment member;

moving the manipulator assembly along the first surface of the alignment member until the upper surface of the manipulator assembly contacts the elongated protrusion; and moving the manipulator assembly with respect to the alignment member until the second alignment marking on the manipulator assembly is aligned with the first alignment marking of the alignment member.

14. A patient introducer, comprising:

an introducer tube having a curvature that defines a curved path and configured to receive a surgical tool and introduce the surgical tool into a patient via guiding the surgical tool into a port along the curved path;

a body directly connected to each of a distal end and a proximal end of the introducer tube and configured to be connected to the port; and an alignment member directly connected to the body, the alignment member configured to interface with a manipulator assembly of a surgical robotic system and facilitate rotational alignment with the manipulator assembly.

15. The patient introducer of claim 14, further comprising:

a mounting member connectable to a patient bed, the mounting member defining a position of the patient introducer with respect to the patient bed, wherein:

the manipulator assembly comprises an electro-magnetic (EM) sensor, the EM sensor configured to sense an EM field generated by an EM generator arranged on or adjacent to the patient bed based on a positioning of the EM sensor relative to the EM generator.

16. The patient introducer of claim 14, wherein the alignment member comprises an acoustic reflector, the acoustic reflector configured to reflect acoustic waves received from an acoustic emitter in the manipulator assembly based on a positioning of the acoustic reflector relative to the acoustic emitter.

17. The patient introducer of claim 14, wherein the alignment member comprises a magnet, the magnet configured to generate a magnetic field based on a positioning of the magnet relative to a magnetic field sensor in the manipulator assembly.

18. The patient introducer of claim 14, wherein the alignment member comprises:

a first surface complementary to a second surface of the manipulator assembly;

an elongated protrusion complementary to an upper surface of the manipulator assembly; and at least one first marking positioned on the alignment member to facilitate rotational alignment with at least one second marking on the manipulator assembly.

19. The patient introducer of claim 14, wherein the alignment member comprises a surface with at least three protrusions, the at least three protrusions configured to be inserted into at least three corresponding features in the manipulator assembly.

20. The patient introducer of claim 19, wherein:

the manipulator assembly further comprises at least three markings corresponding to distal ends of the at least three protrusions of the alignment member, and wherein alignment of the at least three protrusions with the at least three features occurs when each of the protrusions of the alignment member is in contact with a corresponding marking on the manipulator assembly.

21. The patient introducer of claim 14, wherein:

the alignment member defines a hollow cavity comprising a complementary shape to a protrusion in the manipulator assembly, and rotational alignment of the alignment member with the manipulator assembly occurs when, in use, the protrusion of the manipulator assembly is fully inserted into the cavity.

22. The patient introducer of claim 14, wherein:

the introducer tube is configured to be connected to the port via the body.

23. A surgical robotic system, comprising:

a robotic arm; and a manipulator assembly attached to a distal portion of the robotic arm, the manipulator assembly configured to control a surgical tool for insertion into a patient introducer, wherein the manipulator assembly is configured to interface with an alignment member of the patient introducer and facilitate rotational alignment with the patient introducer, and wherein the patient introducer comprises:

an introducer tube extending between (i) a distal end configured to be connected to a port and (ii) a proximal end configured to receive the surgical tool, the introducer tube having a curvature that defines a curved path and configured to introduce the surgical tool into a patient via guiding the surgical tool into the port along the curved path, a body directly connected to each of the distal end and the proximal end of the introducer tube, and an alignment member directly connected to the body and comprising a first shape and a first alignment marking, the alignment member configured to interface with the manipulator assembly, the manipulator assembly comprising a second shape and a second alignment marking, the first shape being complementary to the second shape, wherein the first alignment marking of the alignment member, when aligned with the second alignment marking, facilitates rotational alignment of the alignment member and the manipulator assembly.

24. The surgical robotic system of claim 23, wherein the manipulator assembly comprises a radio-frequency identification (RFID) reader, the RFID reader configured to receive an RFID signal from an RFID tag in the patient introducer based on a positioning of the RFID reader relative to the RFID tag.

25. The surgical robotic system of claim 24, wherein a peak in the strength of the RFID signal is indicative of the manipulator assembly being aligned with the patient introducer.

26. The surgical robotic system of claim 23, wherein the manipulator assembly comprises a laser emitter and a laser sensor, the laser sensor configured to sense laser light emitted from the laser emitter and reflected by a laser reflector in the patient introducer based on a positioning of the laser emitter relative to the laser reflector.

27. The surgical robotic system of claim 23, wherein the manipulator assembly comprises a laser emitter, the laser emitter configured to emit a beam of laser light onto an alignment marking on the alignment member based on a positioning of the laser emitter relative to the alignment marking.

28. The surgical robotic system of claim 23, wherein the manipulator assembly comprises a magnetic field sensor, the magnetic field sensor configured to sense a magnetic field generated by a magnet in the patient introducer based on a positioning of the magnetic field sensor relative to the magnet.

29. The surgical robotic system of claim 23, further comprising:
   an input device configured to receive an input command to begin alignment of the manipulator assembly with the patient introducer,
   wherein the manipulator assembly is configured to be placed into an alignment position in response to the input device receiving the input command.

30. The surgical robotic system of claim 23, further comprising:
   a processor; and
   a memory storing instructions which, when executed by the processor, cause the processor to store an alignment position of the robotic arm in response to the manipulator assembly being aligned with the patient introducer.

* * * * *